United States Patent [19]

Holton

[11] Patent Number: 6,069,260

[45] Date of Patent: May 30, 2000

[54] METAL ALKOXIDES

[75] Inventor: Robert A. Holton, Tallahassee, Fla.

[73] Assignee: Florida State University, Tallahasse, Fla.

[21] Appl. No.: 08/941,640

[22] Filed: Sep. 30, 1997

Related U.S. Application Data

[62] Division of application No. 08/483,309, Jun. 7, 1995, Pat. No. 5,723,634, which is a continuation of application No. 08/314,532, Sep. 28, 1994, Pat. No. 5,466,834, which is a continuation-in-part of application No. 07/949,107, Sep. 22, 1992, abandoned, which is a continuation-in-part of application No. 07/863,849, Apr. 6, 1992, abandoned, which is a continuation-in-part of application No. 07/862,955, Apr. 3, 1992, abandoned, which is a continuation-in-part of application No. 07/763,805, Sep. 23, 1991, abandoned.

[51] Int. Cl.$^7$ .............................................. C07D 305/14
[52] U.S. Cl. ........................................ 549/510; 549/511
[58] Field of Search ...................................... 549/510, 511

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,924,012 | 5/1990 | Colin et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |
| 5,136,060 | 8/1992 | Holton | 549/510 |
| 5,175,315 | 12/1992 | Holton | 549/510 |
| 5,229,526 | 7/1993 | Holton | 549/213 |
| 5,274,124 | 12/1993 | Holton | 549/214 |
| 5,430,160 | 7/1995 | Holton | 549/510 |
| 5,723,634 | 3/1998 | Holton | 549/510 |

FOREIGN PATENT DOCUMENTS

| | | |
|---|---|---|
| 0 247 378 | 4/1986 | European Pat. Off. . |
| 0 253 738 | 7/1986 | European Pat. Off. . |
| 0 253 739 | 7/1986 | European Pat. Off. . |
| 0 336 840 | 4/1988 | European Pat. Off. . |
| 0 336 841 | 4/1988 | European Pat. Off. . |
| 0 400 971 | 5/1989 | European Pat. Off. . |
| 92/09589 | 11/1991 | WIPO . |

OTHER PUBLICATIONS

Bartholomew et al., "A Novel Rearrangement Reaction Conversion of 3–(Chloromethyl)azetidin–2–ones to Azetidine–3–Carboxylic Acid Esters" *Tetrahedron Letters*, vol. 32, No. 36 (1981), pp. 4795–4798.

Denis et al., "A Highly Efficient, Practical Approach To Natural Taxol" *Journal of American Chemical Society*, vol. 110 (1988), pp. 5917–5919.

Deutsch et al., "Synthesis Of Congeners And Prodrugs. 3. Water–Soluble Prodrugs Of Taxol With Potent Antitumor Activity", *J. of Med. Chem.*, 32:4 (1989) pp. 788–792.

Chen et al., "Taxol Structure–Activity Relationships: Synthesis and Biological Evaluation of 2–Deoxytaxol" *Tetrahedron Letters* vol. 34, No. 20, pp. 3205–3206 (1993).

Farina et al., "The Chemistry Of Taxanes: Unexpected Rearrangement of Baccatin III During Chemoselective Debenzoylation With Bu$_3$SnOMe/LiCl", *Tetrahedron Letters* vol. 33, No. 28, pp. 3979–3982. (1992).

Holton et al., "A Synthesis Of Taxusin", *Journal Of The American Chemical Society*, vol. 110 (1988), pp. 6558–6560.

Holton, "Synthesis Of The Taxane Ring System", *Journal Of The American Chemical Society*, vol. 106 (1984), pp. 5731–5732.

Kaiser et al., "Synthesis Of Esters Of Acid–Unstable Alcohols By Meand of n–Butyllithium", *Journal of Organic Chemistry*, vol. 35 (1970), pp. 1198–1199.

L. Klein, "Synthesis of 9–Dihydrotaxol: A Novel Bioactive Taxane", *Tetrahedron Letters* vol. 34, No. 13, pp. 2047–2050, 1993.

Magri et al. "Modified Taxols, 4. Synthesis And Biological Activity Of Taxols Modified In The Side Chain", *Journal of Natural Products*, vol. 51, No. 2 (1988), pp. 298–306.

Mukerjee et al., "β–Lactams: Retrospect and Prospect" *Tetrahedron*, vol. 34 (1978), pp. 1731–1767.

Ojima et al., "New And Efficient Approaches To The Semisyn–thesis Of Taxol And Its C–13 Side Chain Analogs By Means Of β–Lactam Synthon Method", *Tetrahedron*, vol. 48, No. 34 (1992) pp. 6985–7012.

Palomo et al., "Highly Stereoselective Synthesis Of α–Hydroxy β–Amino Acids Through β–Lactams: Application to The Synthesis Of The Taxol and Bestatin Side Chains And Related Systems", *Tetrahedron Let.*, vol. 31, No. 44 (1990), pp. 6429.

Samaranayake et al., "Modified Taxols. 5. Reaction Of Taxol With Electrophilic Reagents And Preparation Of A Rearranged Taxol Derivative With Tubulin Assembly Activity", *Journal Of Organic Chemistry*, vol. 56 (1991), pp. 5114–5119.

Schultz et al., "Synthesis Of New N–Radicals Of Tetrazan––l–yl", *Chemical Abstracts*, vol. 108, No. 37298C (1988), p. 581.

V. Senilh et al., Hemisynthese de nouveaux analogues du taxol. Etude de leur interaction avec la tubuline, *C.R. Acad Sc. Paris*, Serie II, vol. 299, No. 15, pp. 1039–1043, Nov. 21, 1984.

Wani et al., "Plant Antitumor Agents. VI. The Isolation And Structure Of Taxol, A Novel Antileukemic And Antitumor Agent From Taxus Brevifolia", *Journal of American Chemical Society*, vol. 93, No. 9 (May 5, 1971), pp. 2325–2327.

Witherup et al. "High Performance Liquid Chromatographic Separation Of Taxol And Related Compounds From Taxus Brevifolia", *Journal Of Liquid Chromatography*, vol. 12, No. 11 (1989), pp. 2117–2132.

(List continued on next page.)

*Primary Examiner*—Ba K. Trinh
*Attorney, Agent, or Firm*—Senniger, Powers, Leavitt & Roedel

[57] ABSTRACT

A process for preparing N-acyl, N-sulfonyl and N-phosphoryl substituted isoserine esters in which a metal alkoxide is reacted with a β-lactam.

53 Claims, No Drawings

OTHER PUBLICATIONS

W.R. Chan, et al., "Taxa–4(16), 11–diene–5α, 9α, 10α, 13α–tetraol, a New Taxane Derivative from the Heartwood of Yew (*T. baccata* L.):X–Ray Analysis of a p–Bromobenzoate Derivative", *Chem. Commun.* 923 (1966).

Della Casa De Marcano, et al. "The Isolation of Seven New Taxane Derivatives from the Heartwood of Yew (*Taxus baccata* L.)", *Chem. Commun.* 1281 (1969).

Ettouati, L., et al. "Plantes de Nouvelle–Calédonie. 114. Taxanes isolés des feuilles d'*Austrotaxus spicata* Compton (Taxacées)", *Bull. Soc. Chim.* France 749 (1988).

Kingston, D.G.I., et al. "The Taxane Diterpenoids," Progress in the Chemistry of Organic Natural Products, Wein, N.Y., Springer–Verlag, 1993.

Kingston, D.G.I., et al. "New Taxanes from Taxus Brevifolia", *J. Nat Prod.* 45, 466 (1982).

Liu, C.L., et al. "Constituents of the Heartwood of Taiwan Yew", *Tai'wan Ko'hsueh,* vol. 38 (1984) pp. 119–125.

Miller, R.W., et al. "Antileukemic Alkanoids from *Taxus wallichiana Zucc.*" *J.Org. Chem.* 46, 1469 (1981).

Yeh, M.K., et al. "Some Taxane Derivatives From the Heartwood of *Taxus Mairei*", *J.Chin. Chem. Soc.* 35, 309 (1988).

Zhang, Z., et al. "Taxanes From *Taxus Yunnanensis*", *Phytochem.* 29, 3673 (1990).

METAL ALKOXIDES

REFERENCE TO RELATED APPLICATIONS

This application is a divisional application of U.S. Ser. No. 08/483,309, filed Jun. 7, 1995, now U.S. Pat. No. 5,723,634 which is a continuation application of U.S. Ser. No. 08/314,532, filed Sep. 28, 1994, now U.S. Pat. No. 5,466,834, which is a continuation-in-part application of U.S. Ser. No. 07/949,107, filed Sep. 22, 1992, now abandoned, which is a continuation-in-part of U.S. Ser. No. 07/863,849, filed Apr. 6, 1992, now abandoned, which is a continuation-in-part application of U.S. Ser. No. 07/862,955, filed Apr. 3, 1992, now abandoned, which is a continuation-in-part application of U.S. Ser. No. 07/763,805, filed Sep. 23, 1991, now abandoned.

BACKGROUND OF THE INVENTION

Three esters of N-acyl phenyl isoserine, taxol, taxotere and cephalomannine have been found to possess significant properties as antitumor agents. This application describes a process for the preparation of N-acyl, N-sulfonyl and N-phosphoryl substituted isoserine esters, in general and to a semi-synthesis for the preparation of taxane derivatives such as taxol, taxotere and other biologically active derivatives involving the use of metal alkoxides and β-lactams, in particular.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has the following structure:

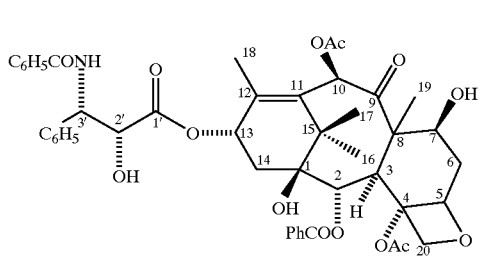

(I)

wherein Ph is phenyl and Ac is acetyl. Because of this promising activity, taxol is currently undergoing clinical trials in both France and the United States.

The supply of taxol for these clinical trials is presently being provided by the bark from *Taxus brevifollia* (Western Yew). However, taxol is found only in minute quantities in the bark of these slow growing evergreens, causing considerable concern that the limited supply of taxol will not meet the demand. Consequently, chemists in recent years have expended their energies in trying to find a viable synthetic route for the preparation of taxol. So far, the results have not been entirely satisfactory.

One synthetic route that has been proposed is directed to the synthesis of the tetracyclic taxane nucleus from commodity chemicals. A synthesis of the taxol congener taxusin has been reported by Holton, et al. in JACS 110, 6558 (1988). Despite the progress made in this approach, the final total synthesis of taxol is, nevertheless, likely to be a multi-step, tedious, and costly process.

A semi-synthetic approach to the preparation of taxol has been described by Greene, et al. in JACS 110, 5917 (1988), and involves the use of a congener of taxol, 10-deacetyl baccatin III which has the structure of formula II shown below:

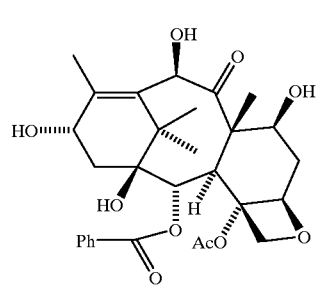

(II)

10-deacetyl baccatin III is more readily available than taxol since it can be obtained from the needles of *Taxus baccata*. According to the method of Greene et al., 10-deacetyl baccatin III is converted to taxol by attachment of the C-10 acetyl group and by attachment of the C-13 β-amido ester side chain through the esterification of the C-13 alcohol with a β-amido carboxylic acid unit. Although this approach requires relatively few steps, the synthesis of the β-amido carboxylic acid unit is a multi-step process which proceeds in low yield, and the coupling reaction is tedious and also proceeds in low yield. However, this coupling reaction is a key step which is required in every contemplated synthesis of taxol or biologically active derivative of taxol, since it has been shown by Wani, et al. in JACS 93, 2325 (1971) that the presence of the β-amido ester side chain at C13 is required for anti-tumor activity.

More recently, it has been reported in Colin et al. U.S. Pat. No. 4,814,470 that taxol derivatives of the formula III below, have an activity significantly greater than that of taxol (I).

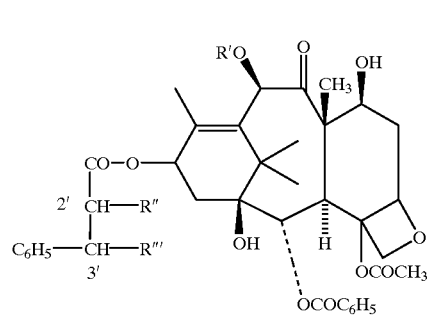

(III)

R' represents hydrogen or acetyl and one of R" and R'" represents hydroxy and the other represents tert-butoxycarbonylamino and their stereoisomeric forms, and mixtures thereof.

According to Colin et al., U.S. Pat. No. 4,418,470, the products of general formula (III) are obtained by the action of the sodium salt of tert-butyl N-chlorocarbamate on a product of general formula:

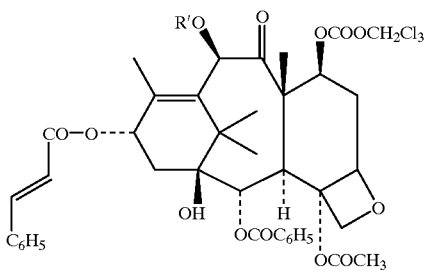

(IV)

in which R' denotes an acetyl or 2,2,2-trichloroethoxycarbonyl radical, followed by the replacement of the 2,2,2-trichloroethoxycarbonyl group or groups by hydrogen. It is reported by Denis et al. in U.S. Pat. No. 4,924,011, however, that this process leads to a mixture of isomers which has to be separated and, as a result, not all the baccatin III or 10-deactylbaccatin III employed for the preparation of the product of general formula (IV) can be converted to a product of general formula (III).

In an effort to improve upon the Colin et al. process, Denis et al. disclose a different process for preparing derivatives of baccatin III or of 10-deactylbaccatin III of general formula

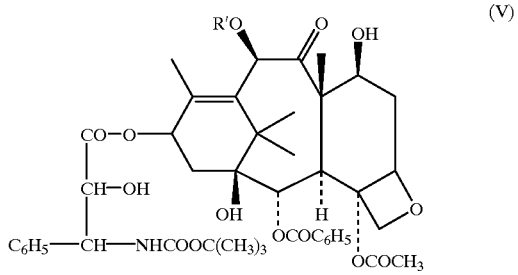

(V)

in which R' denotes hydrogen or acetyl wherein an acid of general formula:

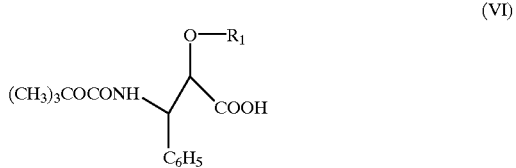

(VI)

in which $R_1$ is a hydroxy-protecting group, is condensed with a taxane derivative of general formula:

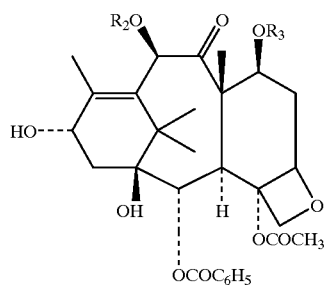

(VII)

in which $R_2$ is an acetyl hydroxy-protecting group and $R_3$ is a hydroxy-protecting group, and the protecting groups $R_1$, $R_3$ and, where appropriate, $R_2$ are then replaced by hydrogen. However, this method employs relatively harsh conditions, proceeds with poor conversion, and provides less than optimal yields.

A major difficulty remaining in the synthesis of taxol and other potential anti-tumor agents is the lack of a readily available method for easy attachment, to the C-13 oxygen, of the chemical unit which provides the β-amido ester side chain. Development of such a process for its attachment in high yield would facilitate the synthesis of taxol as well as related anti-tumor agents having a modified set of nuclear substituents or a modified C-13 side chain. This need has been fulfilled by the discovery of a new, efficient process for attachment, to the C-13 oxygen, of the chemical unit which provides the β-amido ester side chain.

Another major difficulty encountered in the synthesis of taxol is that known processes for the attachment of the β-amido ester side chain at C-13 are generally not sufficiently diastereoselective. Therefore the side chain precursor must be prepared in optically active form to obtain the desired diastereomer during attachment. The process of this invention, however, is highly diastereoselective, thus permitting the use of a racemic mixture of side chain precursor, eliminating the need for the expensive, time-consuming process of separating the precursor into its respective enantiomeric forms. The reaction additionally proceeds at a faster rate than previous processes, thus permitting the use of less side-chain precursor than has been required by such previous processes.

SUMMARY OF THE INVENTION

Among the objects of the present invention, therefore, is the provision of a process for the preparation of N-acyl, N-sulfonyl and N-phosphoryl esters of isoserine; the provision of a side chain precursor for the synthesis of taxane derivatives; the provision of a process for the attachment of the side chain precursor in relatively high yield to provide an intermediate which is readily converted to the desired taxane derivative; and the provision of such a process which is highly diastereoselective.

In accordance with the present invention, a process is provided for the preparation of isoserine esters having the formula

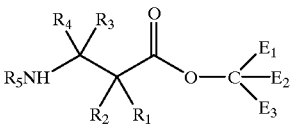

comprising reacting a β-lactam with a metal alkoxide, the β-lactam having the formula

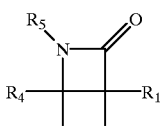

and the metal alkoxide having the formula

wherein
$R_1$ is $-OR_6$, $-SR_7$, or $-NR_8R_9$;

$R_2$ is hydrogen, alkyl, alkenyl, alkynyl, aryl, or heteroaryl;

$R_3$ and $R_4$ are independently hydrogen, alkyl, alkenyl, alkynyl, aryl, heteroaryl, or acyl, provided, however, that $R_3$ and $R_4$ are not both acyl;

$R_5$ is —$COR_{10}$, —$COOR_{10}$, —$COSR_{10}$, —$CONR_8R_{10}$, —$SO_2R_{11}$, or —$POR_{12}R_{13}$, $R_6$ is hydrogen, alkyl, alkenyl, alkynyl, aryl, heteroaryl, hydroxy protecting group, or a functional group which increases the water solubility of the taxane derivative, $R_7$ is alkyl, alkenyl, alkynyl, aryl, heteroaryl, or sulfhydryl protecting group, $R_8$ is hydrogen, alkyl, alkenyl, alkynyl, aryl, or heteroaryl;

$R_9$ is an amino protecting group;

$R_{10}$ is alkyl, alkenyl, alkynyl, aryl, or heteroaryl, $R_{11}$ is alkyl, alkenyl, alkynyl, aryl, heteroaryl, —$OR_{10}$, or —$NR_8R_{14}$, $R_{12}$ and $R_{13}$ are independently alkyl, alkenyl, alkynyl, aryl, heteroaryl, —$OR_{10}$, or —$NR_8R_{14}$, $R_{14}$ is hydrogen, alkyl, alkenyl, alkynyl, aryl, or heteroaryl;

$E_1$, $E_2$ and $E_3$ are independently hydrogen, hydrocarbon or cyclic, provided, at least one of $E_1$, $E_2$ and $E_3$ is other than hydrogen. Preferably, two of $E_1$, $E_2$, and $E_3$ together with the carbon to which they are attached comprise a mono- or polycyclic skeleton.

In accordance with another aspect of the present invention, the metal alkoxide and β-lactam are selected so as to provide a process for preparing taxol, taxotere and other biologically active taxane derivatives having the following structural formula:

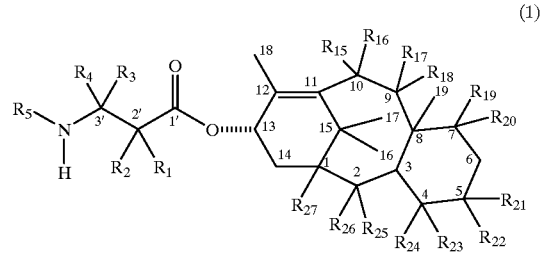

(1)

wherein $R_1$–$R_{14}$ are as previously defined, $R_{15}$ and $R_{16}$ are independently hydrogen, hydroxy, lower alkanoyloxy, alkenoyloxy, alkynoyloxy, aryloyloxy or $R_{15}$ and $R_{16}$ together form an oxo;

$R_{17}$ and $R_{18}$ are independently hydrogen or lower alkanoyloxy, alkenoyloxy, alkynoyloxy, or aryloyloxy or $R_{17}$ and $R_{18}$ together form an oxo;

$R_{19}$ and $R_{20}$ are independently hydrogen or hydroxy or lower alkanoyloxy, alkenoyloxy, alkynoyloxy, or aryloyloxy;

$R_{21}$ and $R_{22}$ are independently hydrogen or lower alkanoyloxy, alkenoyloxy, alkynoyloxy, or aryloyloxy or $R_{21}$ and $R_{22}$ together form an oxo;

$R_{24}$ is hydrogen or hydroxy or lower alkanoyloxy, alkenoyloxy, alkynoyloxy, or aryloyloxy; or $R_{23}$ and $R_{24}$ together form an oxo or methylene or $R_{23}$ and $R_{24}$ together with the carbon atom to which they are attached form an oxirane ring or $R_{23}$ and $R_{22}$ together with the carbon atom to which they are attached form an oxetane ring;

$R_{25}$ is hydrogen, hydroxy, or lower alkanoyloxy, alkenoyloxy, alkynoyloxy, or aryloyloxy or $R_{26}$ is hydrogen, hydroxy, or lower alkanoyloxy, alkenoyloxy, alkynoyloxy, or aryloyloxy; or $R_{26}$ and $R_{25}$ taken together form an oxo; and $R_{27}$ is hydrogen, hydroxy or lower alkoxy, alkanoyloxy, alkenoyloxy, alkynoyloxy, or aryloyloxy.

Briefly, therefore, the taxane derivatives are prepared by reacting a β-lactam (2) with a metal alkoxide having the bi-, tri- or tetracyclic taxane nucleus to form a β-amido ester intermediate. The intermediate is then converted to the taxane derivative. β-lactam (2) has the general formula:

(2)

wherein $R_1$–$R_5$ are as previously defined. The metal alkoxide preferably has the tricyclic taxane nucleus corresponding to the general formula:

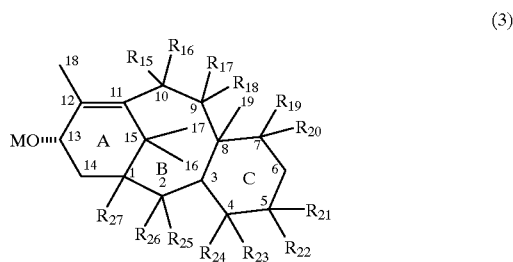

(3)

wherein M is a metal, and $R_{15}$-$R_{27}$ are as previously defined. Most preferably, the metal alkoxide has the tetracyclic taxane nucleus corresponding to metal alkoxide (3) wherein $R_{22}$ and $R_{23}$ together form an oxetane ring.

Other objects and features of this invention will be in part apparent and in part pointed out hereinafter.

DETAILED DESCRIPTION

The present invention is directed to a process for preparing substituted isoserine esters, in general, and taxol, taxotere and other taxane derivatives which are biologically active using β-lactam (2), the structure of which is depicted hereinbelow:

(2)

wherein $R_1$, $R_2$, $R_3$, $R_4$ and $R_5$ are as previously defined.

In accordance with the present invention, $R_5$ of β-lactam (2) is preferably —$COR_{10}$ with $R_{10}$ with $R_{10}$ being aryl, heteroaryl, p-substituted phenyl, or lower alkoxy, and most preferably phenyl, methoxy, ethoxy, tert-butoxy ("tBuO"; $(CH_3)_3CO$—), or

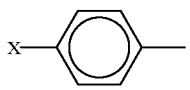

wherein X is Cl, Br, F, CH₃O—, or NO₂—. Preferably $R_2$ and $R_4$ are hydrogen or lower alkyl. $R_3$ is preferably aryl, most preferably, naphthyl, phenyl,

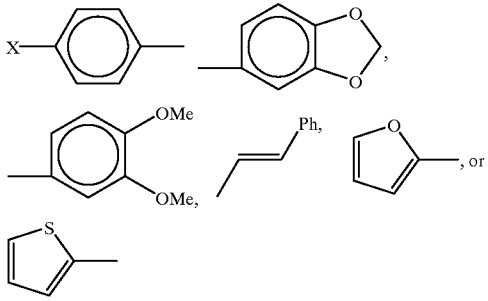

wherein X is as previously defined, Me is methyl and Ph is phenyl. Preferably, $R_1$ is selected from —$OR_6$, —$SR_7$ or —$NR_8R_9$ wherein $R_6$, $R_7$ and $R_9$, are hydroxy, sulfhydryl, and amine protecting groups, respectively, and $R_8$ is hydrogen, alkyl, alkenyl, alkynyl, aryl, or heteroaryl. Most preferably, $R_1$ is —$OR_6$ wherein $R_6$ is triethylsilyl ("TES"), 1-ethoxyethyl ("EE") or 2,2,2-trichloroethoxymethyl.

The β-lactam alkyl groups, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The β-lactam alkenyl groups, either alone or with the various substituents defined hereinabove are preferably lower alkenyl containing from two to six carbon atoms in the principal chain and tip to 15 carbon atoms. They may be straight or branched chain and include ethenyl, propenyl, isopropenyl, butenyl, isobutenyl, aryl, hexenyl, and the like.

The β-lactam alkynyl groups, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

The β-lactam aryl moieties described, either alone or with various substituents, contain from 6 to 15 carbon atoms and include phenyl, α-naphthyl or β-naphthyl, etc. Substituents include alkanoxy, protected hydroxy, halogen, alkyl, aryl, alkenyl, acyl, acyloxy, nitro, amino, amido, etc. Phenyl is the more preferred aryl.

As noted above, $R_1$ of β-lactam (2) may be —$OR_6$ with $R_6$ being alkyl, acyl, ethoxyethyl ("EE"), triethylsilyl ("TES"), 2,2,2-trichloroethoxymethyl, or other hydroxyl protecting group such as acetals and ethers, i.e., methoxymethyl ("MOM"), benzyloxymethyl; esters, such as acetates; carbonates, such as methyl carbonates; and alkyl and acyl silyl such as triethylsilyl, trimethylsilyl, dimethyl-t-butylsilyl, dimethylarylsilyl, dimethyl-heteroarylsilyl, and triisopropylsilyl, and the like. A variety of protecting groups for the hydroxyl group and the synthesis thereof may be found in "Protective Groups in Organic Synthesis" by T. W. Greene, John Wiley and Sons, 1981. The hydroxyl protecting group selected should be easily removed under conditions that are sufficiently mild, e.g., in 48% HF, acetonitrile, pyridine, or 0.5% HCl/water/ethanol, and/or zinc, acetic acid so as not to disturb the ester linkage or other substituents of the taxol intermediate. However, $R_6$ is preferably triethylsilyl, 1-ethoxyethyl or 2,2,2-trichloroethoxymethyl, and most preferably triethylsilyl.

Also as noted previously, $R_7$ may be a sulfhydryl protecting group and $R_9$ may be an amine protecting group. Sulfhydryl protecting groups include hemithioacetals such as 1-ethoxyethyl and methoxymethyl, thioesters, or thiocarbonates. Amine protecting groups include carbamates, for example, 2,2,2-trichloroethylcarbamate or tertbutylcarbamate. A variety of sulfhydryl and amine protecting groups may be found in the above-identified text by T. W. Greene.

Since β-lactam (2) has several asymmetric carbons, it is known to those skilled in the art that the compounds of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

β-lactam (2) can be prepared from readily available materials, as is illustrated in schemes A and B below:

Scheme A

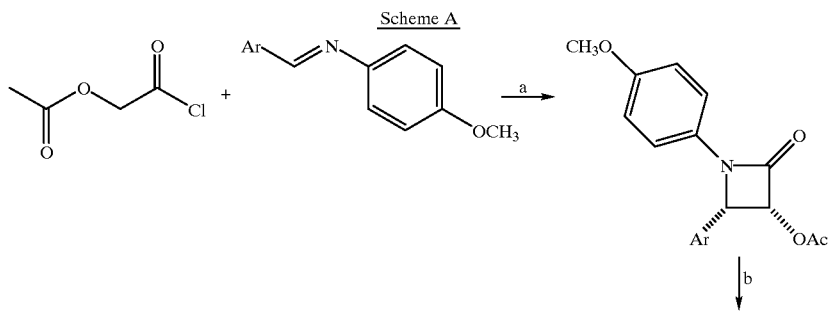

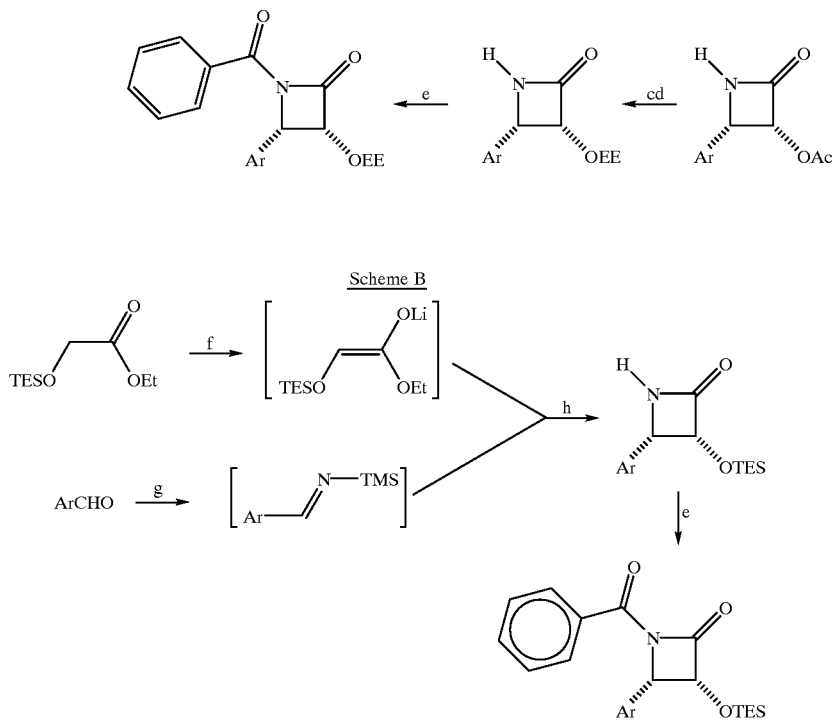

reagents: (a) triethylamine, $CH_2Cl_2$, 25° C., 18 h; (b) 4 equiv ceric ammonium nitrate, $CH_3CN$, –10° C., 10 min; (c) KOH, THF, $H_2O$, 0° C., 30 min; (d) ethyl vinyl ether, THF, toluene sulfonic acid (cat.), 0° C., 1.5 h; (e) n-butyllithium, ether, –78° C., 10 min; benzoyl chloride, –78° C., 1 h; (f) lithium diisopropyl amide, THF –78° C. to –50° C; (g) lithium hexamethyldisilazide, THF –78° C. to 0° C.; (h) THF, –78° C. to 25° C., 12 h.

The starting materials are readily available. In scheme A, α-acetoxy acetyl chloride is prepared from glycolic acid, and, in the presence of a tertiary amine, it cyclocondenses with imines prepared from aldehydes and p-methoxyaniline to give 1-p-methoxyphenyl-3-acyloxy-4-arylazetidin-2-ones. The p-methoxyphenyl group can be readily removed through oxidation with ceric ammonium nitrate, and the acyloxy group can be hydrolyzed under standard conditions familiar to those experienced in the art to provide 3-hydroxy-4-arylazetidin-2-ones. The 3-hydroxyl group is protected with 1-ethoxyethyl, but may be protected with variety of standard protecting groups such as the triethylsilyl group or other trialkyl (or aryl) silyl groups. In Scheme B, ethyl-α-triethylsilyloxyacetate is readily prepared from glycolic acid.

The racemic β-lactams may be resolved into the pure enantiomers prior to protection by recrystallization of the corresponding 2-methoxy-2-(trifluoromethyl) phenylacetic esters. However, the reaction described hereinbelow in which the β-amido ester side chain is attached has the advantage of being highly diastereoselective, thus permitting the use of a racemic mixture of side chain precursor.

The 3-(1-ethoxyethoxy)-4-phenylazetidin-2-one of scheme A and the 3-(1-triethylsilyloxy)-4-phenylazetidin-2-one of scheme B can be converted to β-lactam (2), by treatment with a base, preferably n-butyllithium, and an acyl chloride, alkylchloroformate, sulfonyl chloride, phosphinyl chloride or phosphoryl chloride at –78° C. or below.

The process of the present invention is particularly useful for the esterification of mono- or polycyclic metal alkoxides which are represented by the formula

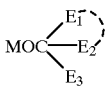

in which $E_1$, $E_2$ and the carbon to which they are attached define a carbocyclic and/or heterocyclic skeleton which may be mono- or polycyclic and $E_3$ is hydrogen or hydrocarbon, preferably lower alkyl. Most preferably, the carbocyclic and/or heterocyclic skeleton comprises about 6 to 20 atoms and the hetero atoms are oxygen. The cyclic skeleton may be hydrocarbon and/or heterosubstituted with heterosubstituents including, for example, esters, ethers, amines, alcohols, protected alcohols, carbonyl groups, halogens, oxygen, substituted oxygen or substituted nitrogen.

When the metal alkoxides have the bi-, tri- or tetracyclic taxane nucleus, the process of the present invention may advantageously be used to prepare taxane derivatives, many of which have been found to have significant biological activity. As used herein, a metal alkoxide having the bicyclic taxane nucleus has the carbocyclic skeleton corresponding to rings A and B of metal alkoxide (3):

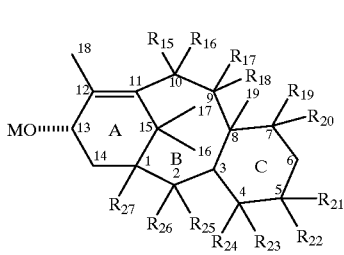
(3)

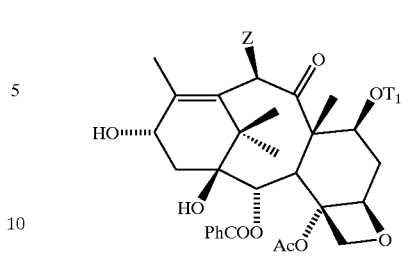
(4)

M and $R_{15}$–$R_{27}$ are as previously defined. A metal alkoxide having the tricyclic taxane nucleus has the carbocyclic skeleton corresponding to rings A, B and C of metal alkoxide (3). A metal alkoxide having the tetracyclic taxane nucleus has carbocyclic rings A, B and C of metal alkoxide (3) and the oxetane ring defined by $R_{22}$, $R_{23}$, and the carbons to which they are attached.

Preferably, the metal alkoxide used in the process of the present invention is metal alkoxide (3). Most preferably, $R_{15}$ is —$OT_2$ or —$OCOCH_3$; $R_{16}$ is hydrogen; $R_{17}$ and $R_{18}$ together form an oxo; $R_{19}$ is —$OT_1$; $R_{20}$ and $R_{21}$ are hydrogen; $R_{22}$ and $R_{23}$ together with the carbons to which they are attached form an oxetane ring; $R_{24}$ is $CH_3COO$—; $R_{25}$ is PhCOO—; $R_{26}$ is hydrogen; $R_{27}$ is hydroxy; and $T_1$ and $T_2$ are independently hydrogen or hydroxy protecting group.

Metal substituent, M, of metal alkoxide (3) is a Group IA, IIA, IIIA, lanthanide or actinide element or a transition, Group IIIA, IVA, VA or VIA metal. Preferably, it is a Group IA, IIA or transition metal, and most preferably, it is lithium, magnesium, sodium, potassium or titanium.

The metal alkoxide alkyl groups, either alone or with the various substituents defined hereinabove are preferably lower alkyl containing from one to six carbon atoms in the principal chain and up to 10 carbon atoms. They may be straight or branched chain and include methyl, ethyl, propyl, isopropyl, butyl, isobutyl, tert-butyl, aryl, hexyl, and the like.

The metal alkoxide alkenyl groups, either alone or with the various substituents defined hereinabove are preferably lower alkenyl containing from two to six carbon atoms in the principal chain and up to 10 carbon atoms. They may be straight or branched chain and include ethenyl, propenyl, isopropenyl, butenyl, isobutenyl, aryl, hexenyl, and the like.

The metal alkoxide alkynyl groups, either alone or with the various substituents defined hereinabove are preferably lower alkynyl containing from two to six carbon atoms in the principal chain and up to 10 carbon atoms. They may be straight or branched chain and include ethynyl, propynyl, butynyl, isobutynyl, aryl, hexynyl, and the like.

Exemplary alkanoyloxy include acetate, propionate, butyrate, valerate, isobutyrate and the like. The more preferred alkanoyloxy is acetate.

The metal alkoxide aryl moieties, either alone or with various substituents contain from 6 to 10 carbon atoms and include phenyl, α-naphthyl or β-naphthyl, etc. Substituents include alkanoxy, hydroxy, halogen, alkyl, aryl, alkenyl, acyl, acyloxy, nitro, amino, amido, etc. Phenyl is the more preferred aryl.

Metal alkoxides (3) are prepared by reacting an alcohol having two to four rings of the taxane nucleus and a C-13 hydroxyl group with an organometallic compound in a suitable solvent. Preferably, the alcohol is a derivative of baccatin III or 10-deacetyl baccatin III having the structure wherein $T_1$ is a hydroxy protecting group, and Z is —$OT_2$ wherein $T_2$ is acyl, preferably acetyl, or other hydroxy protecting group. Most preferably, the alcohol is a protected baccatin III, in particular, 7-O-triethylsilyl baccatin III (which can be obtained as described by Greene, et al. in JACS 110, 5917 (1988) or by other routes) or 7,10-bis-O-triethylsilyl baccatin III.

As reported in Greene et al., 10-deacetyl baccatin III is converted to 7-O-triethylsilyl-10-deacetyl baccatin III according to the following reaction scheme:

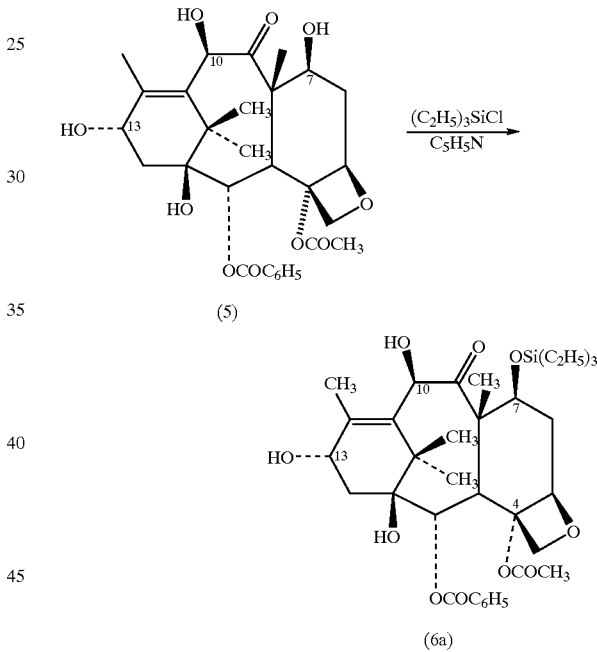

Under what is reported to be carefully optimized conditions, 10-deacetyl baccatin III is reacted with 20 equivalents of $(C_2H_5)_3SiCl$ at 23° C. under an argon atmosphere for 20 hours in the presence of 50 ml of pyridine/mmol of 10-deacetyl baccatin III to provide 7-triethylsilyl-10-deacetyl baccatin III (6a) as a reaction product in 84–86% yield after purification. The reaction product is then acetylated with 5 equivalents of $CH_3COCl$ and 25 mL of pyridine/mmol of (6a) at 0° C. under an argon atmosphere for 48 hours to provide 86% yield of 7-O-triethylsilyl baccatin III (6b). Greene, et al. in JACS 110, 5917 at 5918 (1988).

Alternatively, 7-triethylsilyl-10-deacetyl baccatin III (6a) can be protected at C-10 oxygen with an acid labile hydroxyl protecting group. For example, treatment of (6a) with n-butyllithium in THF followed by triethylsilyl chloride (1.1 mol equiv.) at 0° C. gives 7,10-bis-O-triethylsilyl baccatin III (6c) in 95% yield. Also, (6a) can be converted to 7-O-triethylsilyl-10-(1-ethyloxyethyl) baccatin III (6d) in 90% yield by treatment with excess ethyl vinyl ether and a catalytic amount of methane sulfonic acid. These preparations are illustrated in the reaction scheme below.

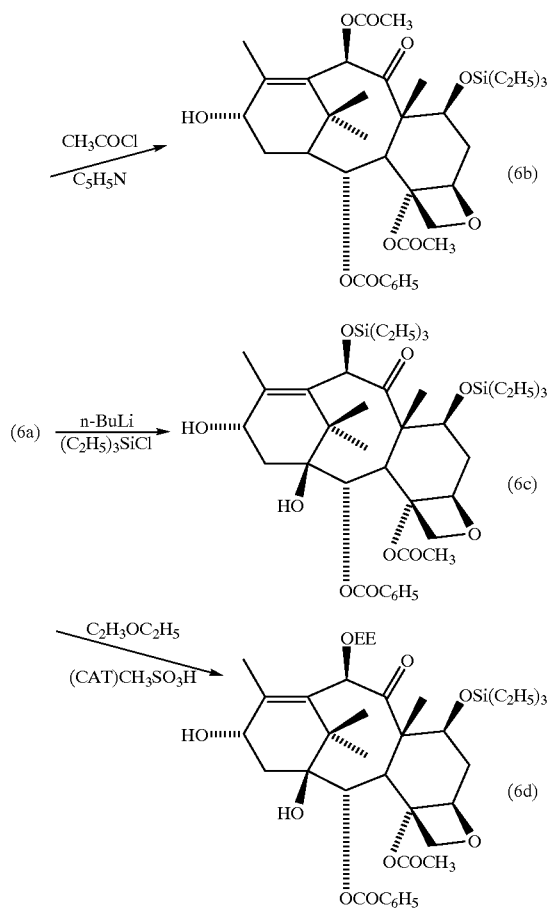

7-O-triethylsilyl baccatin III (6b), 7,10-bis-O-triethylsilyl baccatin III (6c), or 7-O-triethylsilyl-10-(1-ethoxyethyl) baccatin III (6d) is reacted with an organometallic compound such as n-butyllithium in a solvent such as tetrahydrofuran (THF), to form the metal alkoxide 13-O-lithium-7-O-triethylsilyl baccatin III (7b) 13-O-lithium-7,10-bis-O-triethylsilyl baccatin III (7c), or 13-O-lithium-7-O-triethylsilyl-10-(1-ethoxyethyl) baccatin III (7d) as shown in the following reaction scheme:

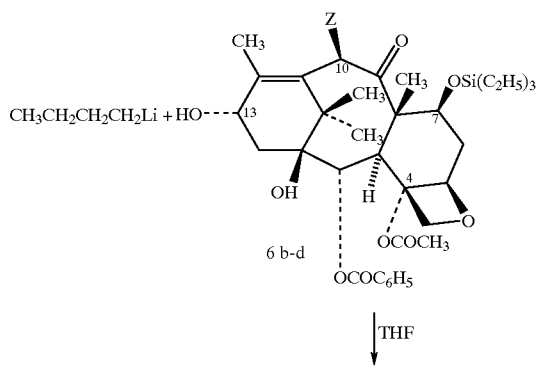

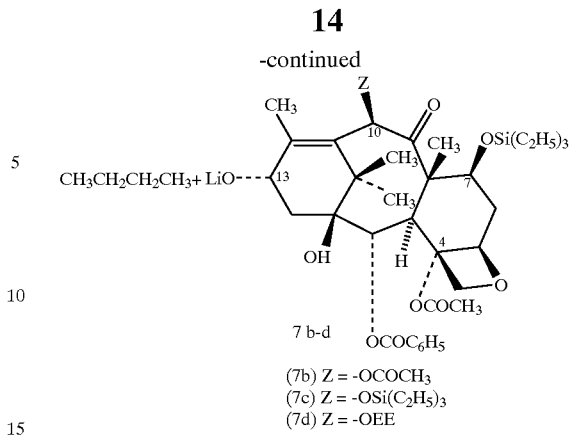

(7b) Z = -OCOCH₃
(7c) Z = -OSi(C₂H₅)₃
(7d) Z = -OEE

As illustrated in the following reaction scheme, a suitable metal alkoxide of the present invention such as 13-O-lithium-7-O-triethylsilyl baccatin III derivative (7b, 7c, or 7d) reacts with a β-lactam of the present invention to provide an intermediate (8b, 8c, or 8d) in which the C-7 hydroxyl group is protected with a triethylsilyl or 1-ethoxyethyl group.

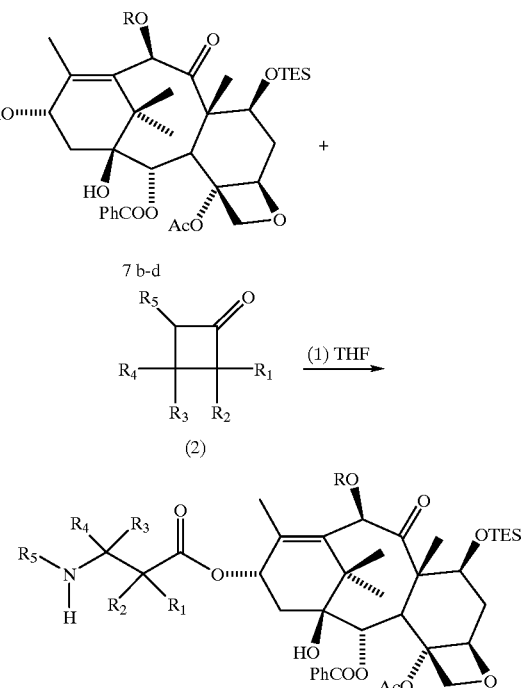

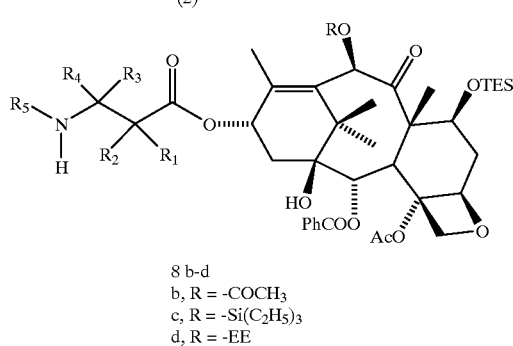

8 b-d
b, R = -COCH₃
c, R = -Si(C₂H₅)₃
d, R = -EE

Intermediate compound (8b) readily converts to taxol when $R_1$ is —$OR_6$, $R_2$ and $R_3$ are hydrogen, $R_4$ is phenyl, $R_5$ is benzoyl and $R_6$ is a hydroxy protecting group such as triethylsilyl. Intermediate compound (8c) readily converts to taxotere when $R_1$ is —$OR_6$, $R_2$ and $R_3$ are hydrogen, $R_4$ is phenyl, $R_5$ is tertbutoxycarbonyl and $R_6$ is a hydroxy protecting group such as triethylsilyl. Intermediate compound (8d) readily converts to 10-deacetyl taxol when $R_1$ is —$OR_6$, $R_2$ and $R_3$ are hydrogen, $R_4$ is phenyl, $R_5$ is benzoyl, and $R_6$ is a hydroxy protecting group such as triethylsilyl. Intermediate compounds (8b, 8c and 8d) may be converted to the indicated compounds by hydrolyzing the triethylsilyl and 1-ethoxyethyl groups under mild conditions so as not to disturb the ester linkage or the taxane derivative substituents.

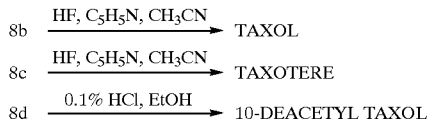

Other taxane derivatives may readily be prepared by selection of the proper substituents $R_1$–$R_5$ of β-lactam (2) or $R_{15}$–$R_{27}$ of metal alkoxide (3). The preparation of such other compounds is illustrated in the examples which follow.

Both the conversion of the alcohol to the metal alkoxide and the ultimate synthesis of the taxol can take place in the same reaction vessel. Preferably, the β-lactam is added to the reaction vessel after formation therein of the metal alkoxide.

The organometallic compound n-butyllithium is preferably used to convert the alcohol to the corresponding metal alkoxide, but other sources of metallic substituent such as lithium diisopropyl amide, other lithium or magnesium amides, ethylmagnesium bromide, methylmagnesium bromide, other organolithium compounds, other organomagnesium compounds, organosodium, organotitanium, organozirconium, organozinc, organocadmium or organopotassium or the corresponding amides may also be used. Organometallic compounds are readily available, or may be prepared by available methods including reduction of organic halides with metal. Lower alkyl halides are preferred. For example, butyl bromide can be reacted with lithium metal in diethyl ether to give a solution of n-butyllithium in the following manner:

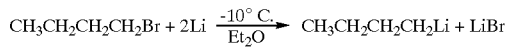

Alternatively, the lithium alkoxide may be induced to undergo exchange with metal halides to form alkoxides of aluminum, boron, cerium, calcium, zirconium or zinc.

Although THF is the preferred solvent for the reaction mixture, other ethereal solvents, such as dimethoxyethane, or aromatic solvents may also be suitable. Certain solvents, including some halogenated solvents and some straight-chain hydrocarbons in which the reactants are too poorly soluble, are not suitable. Other solvents are not appropriate for other reasons. For example, esters are not appropriate for use with certain organometallic compounds such as n-butyllithium due to incompatibility therewith.

Although the reaction scheme disclosed herein is directed to the synthesis of certain taxol derivatives, it can be used with modifications in either the β-lactam or Lie tetracyclic metal alkoxide. Therefore metal alkoxides other than 13-O-lithium-7-O-triethylsilyl baccatin III may be used to form a taxol intermediate according to the method of this invention. The β-lactam and the tetracyclic metal alkoxide can be derived from natural or unnatural sources, to prepare other synthetic taxols, taxol derivatives, 10-deacetyltaxols, and the enantiomers and diastereomers thereof contemplated within the present invention.

The process of the invention also has the important advantage of being highly diastereoselective. Therefore racemic mixtures of the side chain precursors may be used. Substantial cost savings may be realized because there is no need to resolve racemic β-lactams into their pure enantiomers. Additional cost savings may be realized because less side chain precursor, e.g., 60–70% less, is required relative to prior processes.

The water solubility of compounds of formula (1) may be improved if $R_1$ is —$OR_6$ and $R_{19}$ is —$OT_1$, and $R_6$ and/or $T_1$ are a functional group which increases solubility, such as —COGCOR$^1$ wherein G is ethylene, propylene, CHCH, 1,2-cyclohexane, or 1,2-phenylene, $R^1$=OH base, $NR^2R^3$, $OR^3$, $SR^3$, $OCH_2CONR^4R^5$, OH $R^2$=hydrogen, methyl $R^3$=$(CH_2)_n NR^6R^7$; $(CH_2)_n N^{\oplus}R^6R^7R^8 X_1^{\ominus}$ n=1 to 3

$R^4$=hydrogen, lower alkyl containing 1 to 4 carbons $R^5$=hydrogen, lower alkyl containing 1 to 4 carbons, benzyl, hydroxyethyl, $CH_2CO_2H$, dimethylaminoethyl $R^6R^7$=lower alkyl containing 1 or 2 carbons, benzyl or $R^6$ and $R^7$ together with the nitrogen atom of $NR^6R^7$ form the following rings

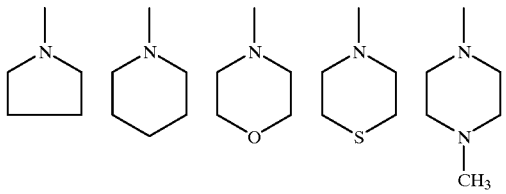

$R^8$=lower alkyl containing 1 or 2 carbons, benzyl $X_1^{\ominus}$=halide base=$NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

The preparation of compounds in which $R_6$ or $T_1$ is —COGCOR$^1$ is set forth in Hangwitz U.S. Pat. No. 4,942,184 which is incorporated herein by reference.

The following examples illustrate the invention.

EXAMPLE 1

Preparation of 2'-ethoxyethyl-7-triethylsilyl Taxol, and Subsequently Taxol, from Racemic β-Lactam To a solution of 7-triethylsilyl baccatin III (20mg, 0.028 mmol) in 1 ml of THF at −78° C. was added dropwise 0.17 ml of a 0.164M solution of nBuLi in hexane. After 30 min at −78° C., a solution of cis-1-benzoyl-3-(1-ethoxyethoxy)-4-phenylazetidin-2-one (47.5 mg, 0.14 mmol) in 1 ml of THF was added dropwise to the mixture. The solution was allowed to slowly warm (over 1.5 h) to 0° C. and was then stirred at 0° C. for 1 h and 1 ml of a 10% solution of AcOH in THF was added. The mixture was partitioned between saturated aqueous $NaHCO_3$ and 60/40 ethyl acetate/hexane. Evaporation of the organic layer gave a residue which was purified by flash chromatography to give 23 mg (80%) of (2'R, 3'S)-2'-ethoxyethyl-7-triethylsilyl taxol and 3.5 mg (13%) of 2',3'-epi(2'S, 3'R)-2'-ethoxyethyl-7-triethylsilyl taxol.

A 5 mg sample of (2'R, 3'S)-2'-ethoxyethyl-7-triethylsilyl taxol was dissolved in 2 ml of ethanol, and 0.5 ml of 0.5% aqueous HCl solution was added. The mixture was stirred at 0° C. for 30 h and diluted with 50 ml of ethyl acetate. The solution was extracted with 20 ml of saturated aqueous sodium bicarbonate solution, dried over sodium sulfate and concentrated. The residue was purified by flash chromatography to provide 4.5 mg (ca. 90%) taxol, which was identical with an authentic sample in all respects.

A 5 mg sample of 2',3'-epi(2'S,3'R)-2'-ethoxyethyl-7-triethylsilyl taxol was dissolved in 2 ml of ethanol and 0.5 ml of 0.5% aqueous HCl solution was added. The mixture was stirred at 0° C. for 30 h and diluted with 50 ml of ethyl acetate. The solution was extracted with 20 ml of saturated aqueous sodium bicarbonate solution, dried over sodium sulfate and concentrated. The residue was purified by flash chromatography to provide 4.5 mg (ca. 90%) of 2',3'-epitaxol.

EXAMPLE 2

Preparation of 2',7-(bis)triethylsilyl Taxol, and Subsequently Taxol, from Racemic β-Lactam To a solution of 7-triethylsilyl baccatin III (100 mg, 0.143 mmol) in 1 ml of THF at −45° C. was added dropwise 0.087 ml of a 1.63M solution of nBuLi in hexane. After 1 h at −45° C., a solution of cis-1-benzoyl-3-triethylsilyloxy-4-phenylazetidin-2-one (274 mg, 0.715 mmol) in 1 ml of THF was added dropwise to the mixture. The solution was allowed to warm to 0° C. and held at 0° C. for 1 h. One ml of a 10% solution of AcOH in THF was added. The mixture was partitioned between saturated aqueous NaHCO$_3$ and 60/40 ethyl acetate/hexane. Evaporation of the organic layer gave a residue which was purified by flash chromatography followed by recrystallization to give 131 mg (85%) of (2'R, 3'S)-2',7-(bis)triethylsilyl taxol and 15 mg (10%) of 2',3'-epi(2'S,3'R)-2',7-(bis)triethylsilyl taxol.

To a solution of 121.3 mg (0.112 mmol) of (2'R, 3'S)-2',7-(bis)triethylsilyl taxol in 6 ml of acetonitrile and 0.3 ml of pyridine at 0° C. was added 0.9 ml of 48% aqueous HF. The mixture was stirred at 0° C. for 8 h, then at 25° C. for 6 h. The mixture was partitioned between saturated aqueous sodium bicarbonate and ethyl acetate. Evaporation of the ethyl acetate solution gave 113 mg of material which was purified by flash chromatography and recrystallization to give 94 mg (98%) taxol, which was identical with an authentic sample in all respects.

To a solution of 5 mg of (2'R, 3'S)-2',7-(bis)triethylsilyl taxol in 0.5 ml of acetonitrile and 0.03 ml of pyridine at 0° C. was added 0.09 ml of 48% aqueous HF. The mixture was stirred at 0° C. for 8 h, then at 25° C. for 6 h. The mixture was partitioned between saturated aqueous sodium bicarbonate and ethyl acetate. Evaporation of the ethyl acetate solution gave 5 mg of material which was purified by flash chromatography and recrystallization to give 4.6 mg (ca. 95%) of 2',3'-epitaxol.

EXAMPLE 3

Preparation of 2',7-(bis)triethylsilyl Taxol, and Subsequently Taxol, from Optically Active β-Lactam To a solution of 7-triethylsilyl baccatin III (100 mg, 0.143 mmol) in 1 ml of THF at −45° C. was added dropwise 0.087 ml of a 1.63M solution of nBuLi in hexane. After 1 h at −45° C., a solution of (+)-cis-1-benzoyl-3-triethylsilyloxy-4-phenylazetidin-2-one (82 mg, 0.215 mmol) in 1 ml of THF was added dropwise to the mixture. The solution was allowed to warm to 0° C. and held at 0° C. for 2 hours. One ml of a 10% solution of AcOH in THF was added. The mixture was partitioned between saturated aqueous NaHCO$_3$ and 60/40 ethyl acetate/hexane. Evaporation of the organic layer gave a residue which was purified by flash chromatography followed by recrystallization to give 145 mg (94%) of (2'R, 3'S)-2',7-(bis)triethylsilyl taxol.

To a solution of 121.3 mg (0.112 mmol) of (2'R, 3'S)-2',7-(bis)triethylsilyl taxol in 6 ml of acetonitrile and 0.3 ml of pyridine at 0° C. was added 0.9 ml of 48% aqueous HF. The mixture was stirred at 0° C. for 8 h, then at 25° C. for 6 h. The mixture was partitioned between saturated aqueous sodium bicarbonate and ethyl acetate. Evaporation of the ethyl acetate solution gave 113 mg of material which was purified by flash chromatography and recrystallization to give 94 mg (98%) taxol, which was identical with an authentic sample in all respects.

EXAMPLE 4

Preparation of Taxotere

To a solution of 7,10-bis-triethylsilyl baccatin III (200 mg, 0.248 mmol)) in 2 mL of THF at −45° C. was added dropwise 0.174 mL of a 1.63M solution of nBuLi in hexane. After 0.5 h at −45° C., a solution of cis-1-(tert-butoxycarbonyl)-3-triethylsilyloxy-4-phenylazetidin-2-one (467 mg, 1.24 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 280 mg of crude 2',7,10-tris-triethylsilyl taxotere.

To a solution of 280 mg of the crude product obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 215 mg of material which was purified by flash chromatography to give 190 mg (95%) of taxotere, which was recrystallized from methanol/water. All analytical and spectral data were identical with that reported for taxotere in U.S. Pat. No. 4,814,470.

EXAMPLE 5

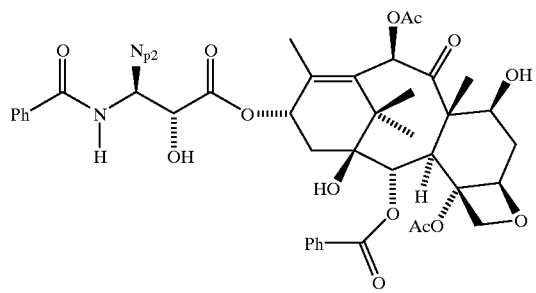

wherein $N_{p2}$ is

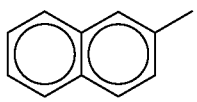

Preparation of 3'-desphenyl-3'-(2-naphthyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(2-naphthyl)azetidin-2-one (620 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 320 mg of a mixture containing (2'R,3'S)-2',7-(bis)triethylsilyl-3'-desphenyl-3'-(2-naphthyl) taxol and a small amount of the (2'S,3'R) isomer.

To a solution of 320 mg (0.283 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 166 mg (64%) of 3'-desphenyl-3'-(2-naphthyl) taxol, which was recrystallized from methanol/water. m.p. 164–165° C; $[\alpha]^{25}_{Na}$ −52.6° (c 0.005, CHCl$_3$).

$^1$H NMR (CDCl$_3$, 300 MHz) δ 8.14 (d, J=7.3 Hz, 2H, benzoate ortho), 7.96 (m, 1H, aromatic), 7.90 (m, 1H, aromatic), 7.85 (m, 2H, aromatic), 7.76 (m, 2H, aromatic), 7.60 (m, 3H, aromatic), 7.52 (m, 4H, aromatic), 7.41 (m, 2H, aromatic), 7.01 (d, J=8.8 Hz, 1H, NH), 6.27 (s, 1H, H10), 6.26 (dd, J=9.2, 9.2 Hz, 1H, H13), 5.97 (dd, J=8.8, 2.5 Hz, 1H, H3'), 5.68 (d, J=7.1 Hz, 1H, H2B), 4.93 (m, 1H, H5), 4.92 (m, 1H, H2'), 4.39 (m, 1H, H7), 4.30 (d, J=8.5 Hz, 1H, H20α), 4.20 (d, J=8.5 Hz, 1H, H20β), 3.81 (d, J=7.1 Hz, 1H, H3), 3.60 (d, J=5 Hz, 1H, 2'OH), 2.48 (m, 1H, H6a), 2.45 (br, 1H, 7OH), 2.39 (s, 3H, 4Ac), 2.30 (m, 2H, H14), 2.24 (s, 3H, 10Ac), 1.83 (in, 1H, H6β), 1.82 (br s, 3H, Me18), 1.68 (s, 1H, 1OH), 1.68 (s, 3H, Me19), 1.24 (s, 3H, Me17), 1.14 (s, 3H, Me16).

EXAMPLE 6

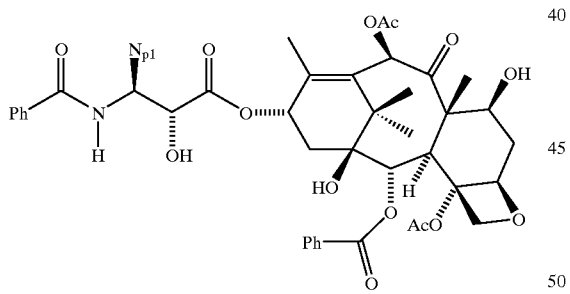

wherein N$_{p1}$ is

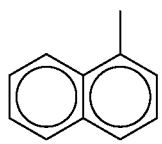

Preparation of 3'-desphenyl-3'-(-naphthyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(1-naphthyl)azetidin-2-one (620 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 325 mg of a mixture containing (2'R,3'S)-2',7-(bis)triethylsilyl-3'-desphenyl-3'-(1-naphthyl) taxol and a small amount of the (2'S,3'R) isomer.

To a solution of 325 mg (0.287 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 166 mg (64%) of 3'-(1-naphthyl) taxol, which was recrystallized from methanol/water. m.p. 164–165° C; $[\alpha]^{25}_{NA}$ −52.6° (c 0.005, CHCl$_3$).

$^1$H NMR (CDCl$_3$, 300 MHz) δ 8.11 (d, J=7.1 Hz, 2H, benzoate ortho), 8.11 (m, 3H, aromatic), 7.91 (m, 3H, aromatic), 7.70 (m, 2H, aromatic), 7.63–7.46 (m, 7H, aromatic), 6.75 (d, J=8.8 HZ, 1H, NH), 6.52 (dd, J=8.8, 1.6 Hz, 1H, H3'), 6.27 (s, 1H, H10), 6.27 (dd, J=9.1, 9.1 Hz, 1H, H13), 5.68 (d, J=7.1 Hz, 1H, H2β), 4.85 (dd, J=7.6, 2.2 Hz, 1H, H5), 4.97 (dd, J=1.6 Hz, 1H, H2'), 4.39 (m, 1H, H7), 4.24 (d, J=8.5 Hz, 1H, H20α), 4.17 (d, J=8.5 Hz, 1H, H20β), 3.80 (d, J=7.1 Hz, 1H, H3), 3.65 (br, 1H, 2'OH), 2.55 (m, 1H, H6α), 2.48 (br, 1H, 7OH), 2.41 (s, 3H, 4Ac), 2.38 (m, 1H, H14), 1.96 (s, 3H, 10Ac), 1.86 (m, 1H, H6β), 1.80 (br s, 3H, Me18), 1.76 (s, 1H, 1OH), 1.69 (s, 3H, Me19), 1.28 (s, 3H, Me17), 1.16 (s, 3H, Me16)

EXAMPLE 7

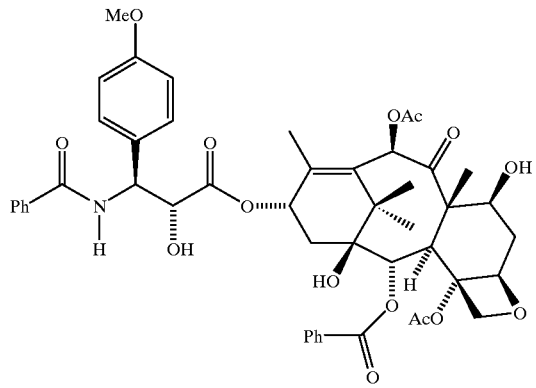

Preparation of 3'-desphenyl-3'-(4-methoxyphenyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-methoxyphenyl)azetidin-2-one (590 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 320 mg of a mixture containing (2=R,3'S)-2',7-(bis)triethylsilyl-3'-desphenyl-3'-(4-methoxyphenyl) taxol and a small amount of the (2'S,3'R) isomer.

To a solution of 320 mg (0.288 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 172 mg (68%) of 3'-desphenyl-3'-(4-methoxyphenyl) taxol, which was recrystallized from methanol/water. m.p. 174–176° C; $[\alpha]^{25}_{Na}$–43.86° (C 0.05, $CHCl_3$).

$^1$H NMR ($CDCl_3$, 300 MHz) δ 8.12 (d, J=7.1 Hz, 2H, benzoate ortho), 7.72 (m, 2H, aromatic), 7.59 (m, 1H, aromatic), 7.53–7.36 (m, 8H, aromatic), 6.96 (d, J=8.8 Hz, 1H, NH), 6.90 (m, 2H, aromatic), 6.26 (s, 1H, H10), 6.21 (dd, J=9.3, 9.3 Hz, 1H, H13), 5.70 (dd, J=8.8, 2.7 Hz, 1H, H3'), 5.66 (d, J=6.8 Hz, 1H, H2β), 4.93 (dd, J=9.9, 2.2 Hz, 1H, H5), 4.74 (dd, J=5.5, 2.7 Hz, 1H, H2'), 4.39 (m, 1H, H7), 4.29 (d, J=8.8 Hz, 1H, H20), 4.18 (d, J=8.8 Hz, 1H, H20β), 3.78 (d, J=6.8 Hz, 1H, H3), 3.78 (s, 3H, ArOMe), 3.67 (d, J=5.5 Hz, 1H, 2'OH), 2.61 (m, 1H, H6α), 2.50 (d, J=4.4 Hz, 1H, 7OH), 2.37 (s, 3H, 4Ac), 2.31 (m, 2H, H14), 2.22 (s, 3H, 10Ac), 1.84 (m, 1H, H6β), 1.79 (br s, 3H, Me18), 1.79 (s, 1H, 1OH), 1.67 (s, 3H, Me19), 1.22 (s, 3H, Me17), 1.13 (s, 3H, Me16).

EXAMPLE 8

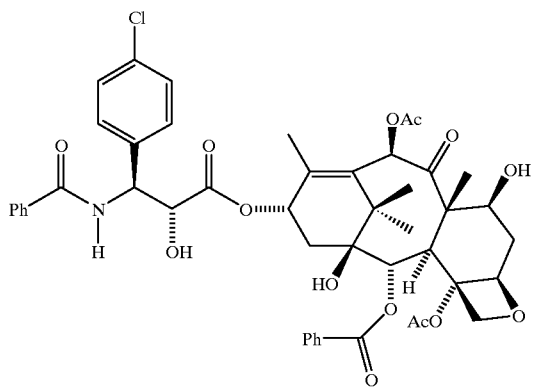

Preparation of 3'-desphenyl-3'-(4-chlorophenyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-Chlorophenyl)azetidin-2-one (595 mg, 1.43 mmol) in 2 mL of THF was added dropwise to the mixture. The solution was warmed to 0° C. and kept at that temperature for 1 h before 1 ml of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 320 mg of a mixture containing (2'R,3'S)-2',7-(bis)triethylsilyl 3'-desphenyl-3'-(4-chlorophenyl) taxol and a small amount of the (2'S,3'R) isomer.

To a solution of 320 mg (0.287 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 158 mg (62%) of 3'-desphenyl-3'-(4-chlorophenyl) taxol, which was recrystallized from methanol/water. m.p. 173–175° C; $[\alpha]^{25}_{Na}$–50.8° (c 0.01, $CHCl_3$).

$^1$H NMR ($CDCl_3$, 300 MHz) δ 8.13 (d, J=7.1 Hz, 2H, benzoate ortho), 7.72 (d, J=8.2 Hz, 2H, benzamide ortho), 7.65–7.35 (m, 1OH, aromatic), 6.97 (d, J=8.8 Hz, 1H, NH), 6.27 (s, 1H, H10), 6.25 (dd, J=8.3, 8.3 Hz, 1H, H13), 5.78 (dd, J=8.8, 2.2 Hz, 1H, H3'), 5.67 (d, J=7.1 Hz, 1H, H2β), 4.95 (dd, J 8.8, 2.2 Hz, 1H, H5), 4.77 (br s, 1H, H2'), 4.40 (m, 1H, H7), 4.31 (d, J=8.2 Hz, 1H, H20α) , 4.19 (d, J=8.2 H , 1H, H20β), 3.80 (d, J=7.1 Hz, 1H, H3), 3.61 (br s, 1H, 2'OH), 2.54 (m, 1H, H6α), 2.38 (s, 3H, 4Ac), 2.32 (m, 2H, H14), 2.24 (s, 3H, 10Ac), 1.85 (m, 1H, H6β), 1.80 (br s, 3H, Me18), 1.68 (s, 3H, Me19), 1.23 (s, 3H, Me17), 1.14 (3, 3H, Me16).

EXAMPLE 9

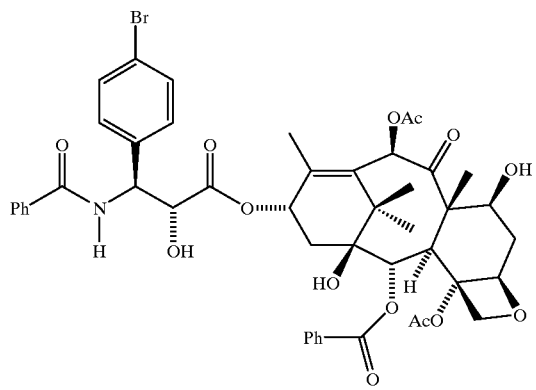

Preparation of 3 '-desphenyl-3'-(4-bromophenyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-bromophenyl)azetidin-2-one (660 mg, 1.43 mmol) In 2 ml of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 330 mg of a mixture containing (2'R,3'S)-2',7-(bis)triethylsilyl-3'-desphenyl-3'-(4-bromophenyl) taxol and a small amount of the (2'S,3'R) isomer.

To a solution of 330 mg (0.284 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 265 mg of material which was purified by flash chromatography to give 186 mg (64%) of 3'-desphenyl-3'-(4-bromophenyl) taxol, which was recrystallized from methanol /water. m.p. 170–172° C; [α]$^{25}_{Na}$–50.94° (c 0.01, CHCl$_3$).

$^1$H NMR (CDCl$_3$, 300 MHz) δ 8.12 (d, J=7.2 Hz, 2H, benzoate ortho), 7.71 (m, 2H, aromatic), 7.61 (m, 1H, aromatic), 7.50–7.47 (m, 6H, aromatic), 7.38 (m, 3H, aromatic), 7.04 (d, J=8.8 Hz, 1H, NH), 6.27 (s, 1H, H10) 6.23 (dd, J=8.2, 8.2 Hz, 1H, H13), 5.75 (dd, J=8.8, 2.2 Hz, 1H, H3'), 5.66 (d, J=7.1 Hz, 1H, H2β), 4.94 (dd, J=9.3, 1.7 Hz, 1H, H5), 4.75 (dd, J=2.2 Hz, 1H, H2'), 4.38 (m, 1H, H7), 4.29 (d, J=8.2 Hz, 1H, H20α), 4.18 (d, J=8.2 Hz, 1H, H20β), 3.79 (d, J=7.1 Hz, 1H, H3), 3.7 (br, 1H, 2'OH), 2.53 (m, 1H, H6α), 2.38 (br, 1H, 7OH), 2.37 (s, 3H, 4Ac), 2.30 (m, 2H, H14), 2.23 (s, 3H, 10Ac), 1.87 (m, 1H, H$_6$β), 1.80 (br s, 3H, Me18), 1.80 (s, 1H, 1OH), 1.67 (s, 3H, Me19), 1.22 (s, 3H, Me17), 1.13 (s, 3H, Me16).

EXAMPLE 10

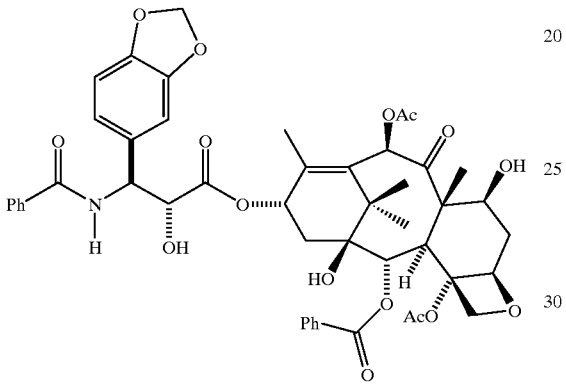

Preparation of 3'-desphenyl-3'-(3,4-methylenedioxyphenyl) Taxol

To a solution of 7-triethylsilyl baccatin III (200 mg, 0.286 mmol) in 2 mL of THF at –45° C. was added dropwise 0.174 mL of a 1.63M solution of nBuLi in hexane. After 0.5 h at –45° C., a solution of cis-1-benzoyl-3-triethylsilyloxy-4-(3,4-methylenedioxyphenyl)azetidin-2-one (610 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 320 mg of a mixture containing (2'R,3'S)-2',7-(bis)triethylsilyl-3'-desphenyl-3'-(3,4-methylenedioxyphenyl) taxol and a small amount of the (2'S,3'R) isomer.

To a solution of 320 mg (0.284 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 113 mg of material which was purified by flash chromatography to give 165 mg (64%) of 3'-desphenyl-3'-(3,4-methylenedioxyphenyl) taxol, which was recrystallized from methanol/water. m.p. 178–180° C; [α]$^{25}_{Na}$–46.6° (c 0.005, CHCl$_3$).

$^1$H NMR (CDCl$_3$, 300 MHz) δ 8.14 (d, J=7.2 Hz, 2H, benzoate ortho), 7.72 (m, 2H, aromatic), 7.15 (m, 1H, aromatic), 7.50 (m, 2H, aromatic), 7.38 (m, 2H, aromatic), 7.0 (m, 1H, aromatic), 6.94 (m, 2H, aromatic), 6.88 (d, J=9.1 Hz, 1H, NH), 6.83 (m, 1H, aromatic), 6.28 (s, 1H, H10), 6.23 (dd, J=9.1, 9.1 Hz, 1H, H13), 5.97 (s, 2H, methylene), 5.69 (dd, J=9.1, 2.5 Hz, 1H, H3'), 5.68 (d, J=6.9 Hz, 1H, H2β), 4.95 (dd, J=9.6, 2.2 Hz, 1H, H5), 4.72 (dd, J=2.5 Hz, 1H, H2'), 4.41 (m, 1H, H7), 4.31 (d, J=8.4 Hz, 1H, H20α), 4.20 (d, J=8.4 Hz, 1H, H20) , 3.81 (d, J=6.9 Hz, 1H, H3), 3.60 (br, 1H, 2'OH), 2.56 (m, 1H, H6α), 2.43 (d, J=4.1 Hz, 1H, 7OH), 2.39 (s, 3H, 4Ac), 2.31 (n, 2H, H14), 2.24 (s, 3H, 10Ac), 1.88 (m, 1H, H6β), 1.82 (br s, 3H, Me18), 1.69 (s, 1H, 1OH), 1.68 (s, 3H, Me19), 1.24 (s, 3H, Me17), 1.15 (s, 3H, Me16).

EXAMPLE 11

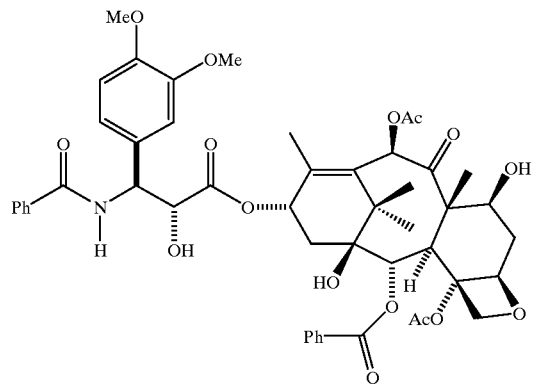

Preparation of 3'-desphenyl-3'-(3,4-dimethoxyphenyl) Taxol

To a solution of 7-triethylsilyl baccatin III (200 mg, 0.286 mmol) in 2 mL of THF at –45° C. was added dropwise 0.174 mL of a 1.63M solution of nBuLi in hexane. After 0.5 h at –45° C., a solution of cis-1-benzoyl-3-triethylsilyloxy-4-(3,4-dimethoxyphenyl)azetidin-2-one (630 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 330 mg of a mixture containing (2'R,3'S)-2',7-(bis)triethylsilyl-3'-desphenyl-3'-(3,4-dimethoxyphenyl) taxol and a small amount of the (2'S,3'R) isomer.

To a solution of 330 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 175 mg (67%) of 3'-desphenyl-3'-(3,4-dimethoxyphenyl) taxol, which was recrystallized from methanol/water. m.p. 165–167° C; [α]$^{25}_{Na}$–42.0° (c 0.005, CHCl$_3$).

$^1$H NMR (CDCl$_3$, 300 MHz) δ 8.12 (d, J=8.3 Hz, 2H, benzoate ortho), 7.73 (d, J=8.2 Hz, 2H, benzamide ortho), 7.65–7.35 (m, 6H, aromatic), 7.1–7.0 (m, 2H, aromatic), 6. 94 (d, J=8.8 Hz, 1H, NH), 6.88 (d, J=8.3 Hz, 2H, aromatic), 6.27 (s, 1H, H10), 6.21 (dd, J=9.3, 9.3 Hz, 1H, H13), 5.69 (m, 2H, H3, H2β), 4.94 (dd, Hz, J=9.9, 2.2 Hz, 1H, H5), 4.77 (d, J=2.8 Hz, 1H, H2'), 4.39 (dd, J=11.0, 6.6 Hz, 1H, H7), 4.30 (d, J=8.5 Hz, 1H, H20α), 4.19 (d, J=8.5 Hz, 1H, H20β), 3.88 (s, 3H, ArOMe), 3.87 (s, 3H, ArOMe), 3.80 (d, J=7.1 Hz, 1H, H3), 3.59 (d, J=4.4 Hz, 1H, 2'OH), 2.54 (m, 1H, H6α), 2.38 (s, 3H, 4Ac), 2.36 (n, 2H, H14α, H14β), 2.23 (s, 3H, 10Ac), 1.86 m, 1H, H6β), 1.80 (br s, 3H, Me18), 1.68 (s, 3H, Me19), 1.23 (s, 3H, Me17), 1.14 (s, 3H, Me16).

EXAMPLE 12

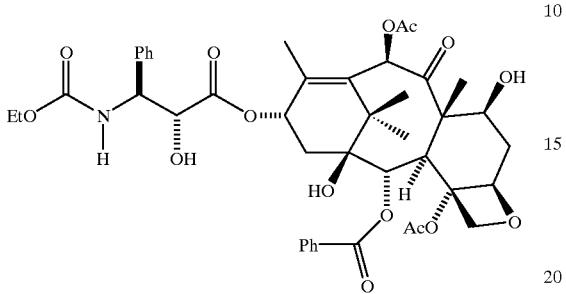

Preparation of N-debenzoyl-N-ethoxycarbonyl Taxol

To a solution of 7-triethylsilyl baccatin III (155 mg, 0.221 mmol)) in 2 mL of THF at −45° C. was added dropwise 0.136 mL of a 1.63M solution of nBuLi in hexane. After 0.5 h at −45° C., a solution of cis-1-ethoxycarbonyl-3-triethylsilyloxy-4-phenylazetidin-2-one (386 mg, 1.11 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 252 mg of a mixture containing (2'R,3'S)-2',7-(bis)triethylsilyl-N-debenzoyl-N-ethoxycarbonyl taxol and a small amount of the (2'S,3'R) isomer.

To a solution of 252 mg (0.112 mmol) of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 216 mg of material which was purified by flash chromatography to give 155 mg (85%) of N-debenzoyl-N-ethoxycarbonyl taxol, which was recrystallized from methanol/water. m.p. 161.5–162.5° C; $[\alpha]^{25}_{Na}$−62.2° (c 0.51, CHCl₃).

¹H NMR (CDCl₃, 300 MHz) δ 8.12 (d, J=7.7 Hz, 2H, benzoate ortho), 7.65–7.3 (m, 8H, aromatic), 6.28 (m, 1H, H10) 6.27(m, 1H, H13) , 5.67 (d, J=7.1 Hz, 1H, H2 ) , 5.53 (d, J=9.3 Hz, 1H, H3'), 5.29 (d, J=9.3 Hz, 1H, NH), 4.94 (dd, J=9.3, 2.2 Hz, 1H, H5), 4.64 (dd, J=5.0, 2.8 Hz, 1H, H2'), 4.41 (m, 1H, H7), 4.29 (d, J=8.5 Hz, 1H, H20α), 4.17 (d, J=8.5 Hz, 1H, H20β), 4.01 (q, J=7.1 Hz, 2H, COO ₂CH₃), 3.79 (d, J=7.1 Hz, 1H, H3), 3.45 (d, J=5 Hz, 1H, 2'OH), 2.54 (m, 1H, H6a), 2.47 (d, J=3.9 Hz 1H, 7OH), 2.36 (s, 3H, 4Ac),2.24 (s, 3H, 10Ac), 2.22 (m, 2H, H14a, H14β), 1.87 (m, 1H, H6α), 1.83 (br s, 3H, Me18), 1.77 (s, 1H, 1OH), 1.68 (s,3H, Me19), 1.27 (s, 3H, Me17), 1.15 (s, 3H, Me16), 1.14 (t, J=7.1 Hz, 2H, COOCH₂CH₃)

EXAMPLE 13

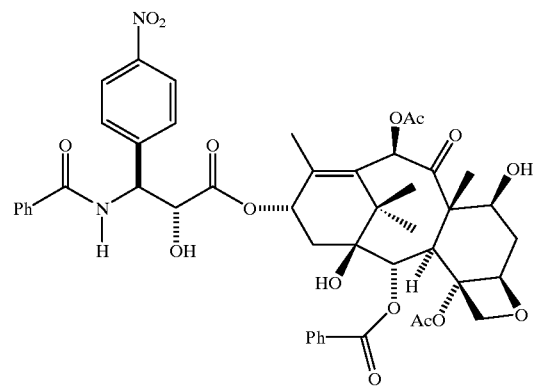

Preparation of 3'-desphenyl-3'-(4-nitrophenyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-nitrophenyl)azetidin-2-one (610 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 320 mg of a mixture containing (2'R,3'S)-2',7-(bis)triethylsilyl-3'-desphenyl-3'-(4-nitrophenyl) taxol and a small amount of the (2'S,3'R) isomer.

To a solution of 320 mg (0.284 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 147 mg (57%) of 3'-desphenyl-3'-(4-nitrophenyl) taxol, which was recrystallized from methanol/water. m.p. 188–190° C; $[\alpha]^{25}_{Na}$−63.7° (c 0.01, CHCl₃).

¹H NMR (CDCl₃, 300 MHz) δ 8.26 (d, J=8.8 Hz, 2H, benzoate ortho), 8.20 (m, 2H, aromatic), 7.73 (m, 4H, aromatic), 7.60 (m, 1H, aromatic), 7.52 (m, 4H, aromatic), 7.41 (m, 1H, aromatic), 7.15 (d, J=8.8 Hz, 1H, NH), 6.26 (s, 1H, H10), 6.26 (dd, J=9.3, 9.3 Hz, 1H, H13), 5.93 (dd, J=8.8, 2.8 Hz, 1H, H3'), 5.66 (d, J=6.6 Hz, 1H H2β), 4.94 (dd, J=9.3, 1.7 Hz, 1H, H5), 4.82 (dd, J=3.9, 2.8 Hz, 1H, H2'), 4.38 (m, 1H, H7), 4.30 (d, J=8.8 Hz, 1H, H20α), 4.19 (d, J=8.8 Hz, 1H, H20β), 3.86 (d, J=3.9 Hz, 1H, 2'OH), 3.79 (d, J=6.6 Hz, 1H, H3), 2.55 (m, 1H, H6α), 2.46 (d, J=3.8 Hz, 1H, 7OH), 2.41 (s, 3H, 4Ac), 2.38 (m, 2H, H14), 2.23 (s, 3H, 10Ac), 1.82 (m, 1H, H6β), 1.80 (br s, 3H, Me18), 1.74 (s, 1H, 1OH), 1.68 (S, 3H, Me19), 1.21 (s, 3H, Me17), 1.13 (s, 3H, Me16).

EXAMPLE 14

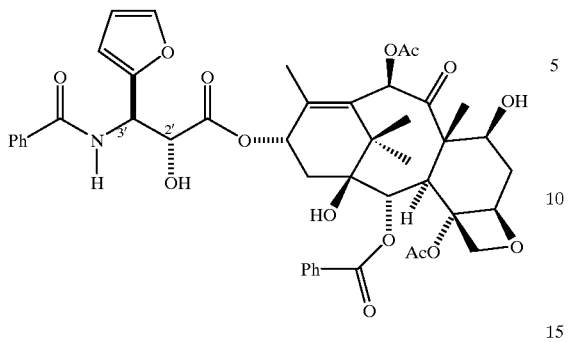

Preparation of 3'-desphenyl-3'-(2-furyl) Taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-benzoyl-3-triethylsilyloxy-4-(2-furyl)azetidin-2-one (266 mg, 0.715 mmol) in 1 ml of THF was added dropwise to the mixture. The solution was warmed to 0° C and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 143 mg of a mixture containing (2'R,3'S)-2',7-(bis)triethylsilyl-3'-desphenyl-3'-(2-furyl) taxol and a small amount of the (2'S,3'R) isomer.

To a solution of 143 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 115 mg of material which was purified by flash chromatography to give 98 mg (81%) of 3'-desphenyl-3'-(2-furyl) taxol, which was recrystallized from methanol/water. m.p. 174–176° C; $[\alpha]^{25}_{Na}$−47.8° (c 0.045, CHCl$_3$).

$^1$H NMR (CDCl$_3$, 300 MHz) δ 8.14 (d, J=7.0 Hz, 2H, benzoate ortho), 7.74 (m, 2H, aromatic), 7.51 (m, 7H, aromatic), 6.86 (d, J=9.2 Hz, 1H, NH), 6.40 (d, J=1.2 Hz, 2H, furyl), 6.29 (s, 1H, H10), 6.24 (dd, J=9.2, 9.2 Hz, 1H, H13), 5.89 (dd, J=9.2, 2.4 Hz, 1H, H3'), 5.69 (d, J=7.0 Hz, 1H, H2β), 4.96 (dd, J=9.5, 1.8 Hz, 1H, H5), 4.83 (d, J=2.4 Hz, 1H, H2'), 4.42 (dd, J=10.7, 6.7 Hz, 1H, H7), 4.31 (d, J=8.6 Hz, 1H, H20α), 4.20 (d, J=8.6 Hz, 1H, H20β), 3.83 (d, J=7.0 Hz, 1H, H3), 2.56 (m, 1H, H6α), 2.43 (s, 3H, 4Ac), 2.35 (m, 2H, H14), 2.24 (s, 3H, 10Ac), 1.89 (m, 1H, H6β), 1.87 (br s, 3H, Me18), 1.87 (s, 1H, 1OH), 1.69 (s, 3H, Me19), 1.25 (s, 3H, Me17), 1.15 (s, 3H, Me16).

EXAMPLE 15

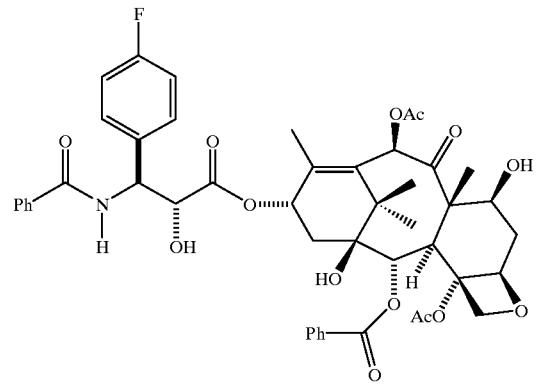

Preparation of 3'-desphenyl-31-(4-fluorophenyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-fluorophenyl)azetidin-2-one (570 mg, 1.43 mmol) in 2 mL of THF was added dropwise to the mixture. The solution was warmed to 0° C. and kept at that temperature for 1 h before 1 mL, of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 315 mg of a mixture containing (2'R,3'S)-2',7-(bis)triethylsilyl-3'-desphenyl-3'-(4-fluorophenyl) taxol and a small amount of the (2'S,3'R) isomer.

To a solution of 315 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 250 mg of material which was purified by flash chromatography to give 160 mg (64%) of 3'-desphenyl-3'-(4-fluorophenyl) taxol, which was recrystallized from methanol/water. m.p. 71–173° C;$[\alpha]^{25}_{Na}$−49.0° (c 0.005, CHCl$_3$).

$^1$H NMR (CDCl$_3$, 300 MHz) δ 8.13 (d, J=7.5 Hz, 2H, benzoate ortho), 7.25 (m, 2H, aromatic), 7.61 (m, 1H, aromatic), 7.50 (m, 4H, aromatic), 7.43 (m, 2H, aromatic), 7.10 (m, 2H, aromatic), 6.96 (d, J=8.7 Hz, 1H, NH), 6.27 (s, 1H, H10), 6.25 (dd, J=8.7, 8.7 Hz, 1H, H13), 5.79 (dd, J=8.7, 2.4 Hz, 1H, H3'), 5.67 (d, J=7.1 Hz, 1H, H2β), 4.45 (dd, J=7.9 Hz, 1H, H5), 4.76 (dd, J=4.8, 2.4 Hz, 1H, H2'), 4.39 (n, 1H, H7), 4.31 (d, J=8.9 Hz, 1H, H20c), 4.20 (d, J=8.9 Hz, 1H, H20β), 3.80 (d, J=7.1 Hz, 1H, H3), 3.57 (d, J=4.8 Hz, 1H, 2'OH), 2.58 (m, 1H, H6a), 2.43 (d, J=4.3 Hz, 1H, 7OH), 2.38 (s, 3H, 4Ac), 2.30 (m, 2H, H14), 2.24 (s, 3H, 10Ac), 1.85 (m, 1H, H6β), 1.80 (br s, 3H, Me18), 1.69 (s, 1H, 1OH), 1.55 (s, 3H, Me19), 1.23 (s, 3H, Me17), 1.14 (s, 3H, Me16).

EXAMPLE 16

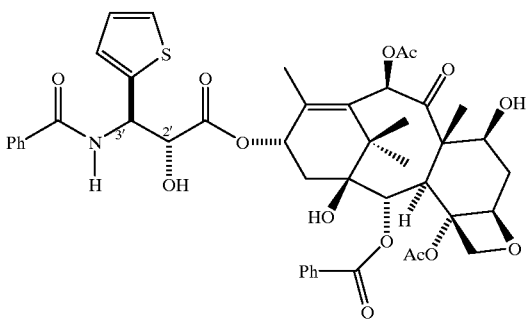

Preparation of 3'-Desphenyl-3'-(2-thienyl) Taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(4-benzoyl)-3-triethylsilyloxy-4-(2-thienyl)azetidin-2-one (277 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 169 mg of a mixture containing (2'R,3'S)-2',7-(bis)triethylsilyl-3'-desphenyl-3'-(2-thienyl) taxol and a small amount of the (2'S,3'R) isomer.

To a solution of 169 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 140 mg of material which was purified by flash chromatography to give 93 mg (76%) of 3'-desphenyl-3'-(2-thienyl) taxol, which was recrystallized from methanol/water. m.p. 173–175° C.; $[\alpha]^{25}_{Na}$−42.1° (c 0.515, CHCl$_3$).

$^1$H NMR (CDCl$_3$, 300 MHz) δ 8.14 (d, J=7.1 Hz, 2H, benzoate ortho), 7.72 (d, J=8.7 Hz, 2H, benzamide ortho), 7.65–7.35 (m, 6H, aromatic), 7.31 (dd, J=5.5, 1.1 Hz, 1H, thienyl), 7.19 (dd, J=3.9, 1.1 Hz, 1H, thienyl), 7.03 (dd, J=5.5, 3.9 Hz, 1H, thienyl), 6.96 (d, J=8.8 Hz, 1H, NH), 6.28 (s, 1H, H10), 6.24 (dd, J=8.8, 7.7 Hz, 1H, H13), 6.05 (dd, J=8.8, 1.7 Hz, 1H, H3'), 5.68 (d, J=7.1 Hz, 1H, H2), 4.95 (dd, J=9.3, 1.7 Hz, 1H, H5), 4.78 (d, J=2.2 Hz, 1H, H2'), 4.40 (dd, J=11.0, 6.6 Hz, 1H, H7), 4.31 (d, J=8.5 Hz, 1H, H20α), 4.20 (d, J=8.5 Hz, 1H, H20β), 3.81 (d, J=7.1 Hz, 1H, H3), 3.72 (br, s, 1H, 2'OH), 2.54 (m, 1H, H6α), 2.41 (s, 3H, 4Ac), 2.37 (m, 2H, H14α, H14β), 2.23 (s, 3H, 10Ac), 1.88 (m, 1H, H6α), 1.82 (br s, 3H, Me18), 1.68 (s, 3H, Me19), 1.23 (s, 3H, Me17), 1.14 (s, 3H, Me16).

EXAMPLE 17

Preparation of 2',7-hydroxy Protected Taxol Using Magnesium Alkoxide

To a solution of 7-triethylsilyl baccatin III (100 mg, 0.143 mmol) in 1 mL of THF at −45° C. was added dropwise 0.048 mL of a 3.0M solution of methyl magnesium bromide in ether. After 1 h at −45° C., a solution of (+)-cis-1-benzoyl-3-triethylsilyloxy-4-phenylazetidin-2-one (82 mg, 0.215 mmol) in 1 mL of THF was added dropwise to the mixture. The solution was warmed to 0° C. and kept at that temperature for 4 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by flash chromatography followed by recrystallization to give 148 mg (96%) of (2'R,3'S)-2',7-(bis)triethylsilyl taxol.

EXAMPLE 18

Preparation of 2',7-hydroxy Protected Taxol Using Potassium Alkoxide

To a solution of 7-triethylsilyl baccatin III (100 mg, 0.143 mmol) in 1 mL of THF at −45° C. was added dropwise 0.286 mL of a 0.5M solution of potassium hexamethyldisilazide in toluene. After 1 h at −45° C., a solution of (+)-cis-1-benzoyl-3-triethylsilyloxy-4-phenylazetidin-2-one (82 mg, 0.215 mmol) in 1 mL of THF was added dropwise to the mixture. The solution was warmed to 0° C. and kept at that temperature for 3 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by flash chromatography followed by recrystallization to give 139 mg (90%) of (2'R,3'S)-2',7-(bis)triethylsilyl taxol.

EXAMPLE 19

Preparation of 2',7-hydroxy Protected Taxol Using Lithium Alkoxide from Lithium Hexamethyldisilazide To a solution of 7-triethylsilyl baccatin III (100 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-triethylsilyloxy-4-phenylazetidin-2-one (82 mg, 0.215 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by flash chromatography followed by recrystallization to give 151 mg (98%) of (2'R,3'S)-2',7-(bis)triethylsilyl taxol.

EXAMPLE 20

Preparation of Taxol Using Lithium Alkoxide (from Lithium Hexamethyldisilazide)

To a solution of 7-triethylsilyl baccatin III (100 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-(2-methoxy-2-propyloxy)-4-phenylazetidin-2-one (58 mg, 0.172 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by recrystallization to give 147 mg (99%) of (2'R, 3'S)-2'-(2-methoxy-2-propyloxy)-7-triethylsilyl taxol.

To a solution of 116 mg (0.112 mmol) of (2'R,3'S)-2'-(2-methoxy-2-propyloxy)-7-triethylsilyl taxol in 6 mL of acetonitrile and 0.3 mL of pyridine at 0° C. was added 0.9 mL of 48% aqueous HF. The mixture was stirred at 0° C. for 8 h, then at 25° C. for 10 h. The mixture was partitioned between saturated aqueous sodium bicarbonate and ethyl acetate. Evaporation of the ethyl acetate solution gave 113 mg of material which was purified by recrystallization to give 95 mg (99%) of taxol, which was identical with an authentic sample in all respects.

EXAMPLE 21

Methyl N-benzoyl-(2'R,3'S)-phenylisoserine Ester

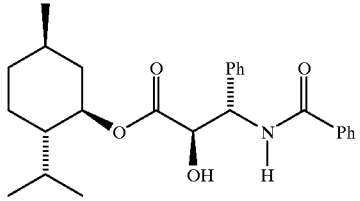

To a solution of (−)-menthol (22 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-(2-methoxy-2-propyloxy)-4-phenylazetidin-2-one (58 mg, 0.172 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave 77 mg of a residue which was dissolved in 6 mL of THF at 0° C. To this solution was added 0.9 mL of glacial acetic acid and 0.9 mL of water. The mixture was stirred at 0° C. for 3 h, then partitioned between saturated aqueous sodium bicarbonate and ethyl acetate. Evaporation of the ethyl acetate solution gave 70 mg of material which was purified by chromatography on silica gel to give 48 mg (80%) of methyl N-benzoyl-(2'R,3'S)-phenylisoserine ester.

EXAMPLE 22

Bornyl N-benzoyl-(2'R,3'S)-phenylisoserine Ester

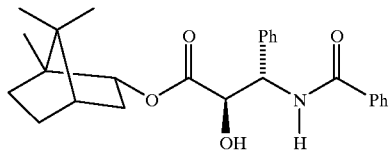

To a solution of (−)-borneol (22 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-(2-methoxy-2-propyloxy)-4-phenylazetidin-2-one (58 mg, 0.172 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave 75 mg of a residue which was dissolved in 6 mL of THF at 0° C. To this solution was added 0.9 mL of glacial acetic acid and 0.9 mL of water. The mixture was stirred at 0° C. for 3 h, then partitioned between saturated aqueous sodium bicarbonate and ethyl acetate. Evaporation of the ethyl acetate solution gave 70 mg of material which was purified by chromatography on silica gel to give 54 mg (90%) of bornyl N-benzoyl-(2'R,3'S)-phenylisoserine ester.

EXAMPLE 23

S-verbenyl N-benzoyl-(2'R,3'S)-phenylisoserine Ester

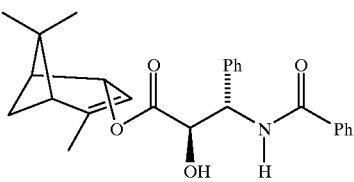

To a solution of S-cis-verbenol (22 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-(2-methoxy-2-propyloxy)-4-phenylazetidin-2-one (58 mg, 0.172 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave 79 mg of a residue with was dissolved in 6 mL of THF at 0° C. To this solution was added 0.9 mL of glacial acetic acid and 0.9 mL of water. The mixture was stirred at 0° C. for 3 h, then partitioned between saturated aqueous sodium bicarbonate and ethyl acetate. Evaporation of the ethyl acetate solution gave 70 mg of material which was purified by chromatography on silica gel to give 55 mg (92%) of S-verbenyl N-benzoyl-(2'R,3'S)-phenylisoserine ester.

EXAMPLE 24

Terpinen-4-yl N-benzoyl-(2'R,3'S)-phenylisoserine Ester

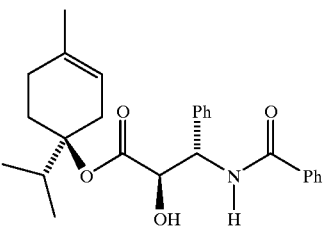

To a solution of (+)-terpinene-4-ol (22 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-(2-methoxy-2-propyloxy)-4-phenylazetidin-2-one (58 mg, 0.172 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave 80 mg of a residue which was dissolved in 6 mL of THF at 0° C. for 3 h, then partitioned between saturated aqueous sodium bicarbonate and ethyl acetate. Evaporation of the ethyl acetate solution gave 70 mg of material which was purified by chromatography on silica gel to give 50 mg (83%) of terpinen-4-yl N-benzoyl-(2'R,3'S)-phenylisoserine ester.

EXAMPLE 25

Isopinocamphenyl N-benzoyl-(2'R,3'S)-phenylisoserine Ester

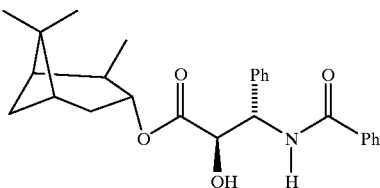

To a solution of (−)-isopinocamphenyl (22 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-(2-methoxy-2-propyloxy)-4-phenylazetidin-2-one (58 mg, 0.172 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave 77 mg of a residue which was dissolved in 6 mL of THF at 0° C. To this solution was added 0.9 mL of glacial acetic acid and 0.9 mL of water. The mixture was stirred at 0° C. for 3 h, then partitioned between saturated aqueous sodium bicarbonate and ethyl acetate. Evaporation of the ethyl acetate solution gave 70 mg of material which was purified by chromatography on silica gel to give 53 mg (89%) of isocamphenyl N-benzoyl-(2'R,3'S)-phenylisoserine ester.

EXAMPLE 26

α-terpineyl N-benzoyl-(2'R,3'S)-phenylisoserine Ester

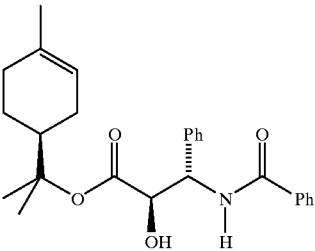

To a solution of (−)-menthol (22 mg, 0.143 mmol) in 1 mL of THF at −45° C. was added dropwise 0.143 mL of a 1.0M solution of lithium hexamethyldisilazide in THF. After 1 h at −45° C., a solution of (+)-cis-1-benzoyl-3-(2-methoxy-2-propyloxy)-4-phenylazetidin-2-one (58 mg, 0.172 mmol) in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave 73 mg of a residue which was dissolved in 6 mL of THF at 0° C. To this solution was added 0.9 mL of glacial acetic acid and 0.9 mL of water. The mixture was stirred at 0° C. for 3 h, then partitioned between saturated aqueous sodium bicarbonate and ethyl acetate. Evaporation of the ethyl acetate solution gave 70 mg of material which was purified by chromatography on silica gel to give 48 mg (80%) of α-terpineyl N-benzoyl-(2'R,3'S)-phenylisoserine ester.

EXAMPLE 27

Preparation of 2',7-hydroxy Protected Taxol Using Sodium Alkoxide

To a solution of 7-triethylsilyl baccatin III (100 mg, 0.143 mmol) in 1 mL of THF at −45° C. is added dropwise 0.143 mL of a 1M solution of sodium hexamethyldisilazide in THF. After 1 h at −45° C., a solution of (+)-cis-1-benzoyl-3-triethylsilyloxy-4-phenylazetidin-2-one (82 mg, 0.215 mmol) in 1 mL of THF is added dropwise to the mixture. The solution is warmed to 0° C. and kept at that temperature for 3 h before 1 mL of a 10% solution of AcOH in THF is added. The mixture is partitioned between saturated aqueous NaHCO$_3$ and 60/40 ethyl acetate/hexane. Evaporation of the organic layer gives a residue which is purified by flash chromatography followed by recrystallization to give 108 mg (70%) of (2'R,3'S)-2',7-(bis)triethylsilyl taxol.

EXAMPLE 28

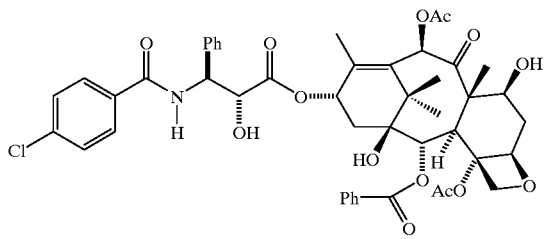

Preparation of N-debenzoyl-N-(4-chlorobenzoyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of (+)-cis-1-(4-chlorobenzoyl)-3-triethylsilyloxy-4-phenylazetidin-2-one (215 mg, 0.515 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 320 mg of crude (2'R,3'S)-2',7-(bis)triethylsilyl-N-debenzoyl-N-(4-chlorobenzoyl) taxol.

To a solution of 320 mg (0.286 mmol) of this crude product in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 252 mg of material which was purified by flash chromatography to give 213 mg (84%) of N-debenzoyl-N-(4-chlorobenzoyl) taxol, which was recrystallized from methanol/water. m.p. 179–181° C.; [α]$^{25}_{Na}$ −49.8° (c 0.01, CHCl$_3$).

¹H NMR (CDCl₃, 300 MHz) δ 8.12 (d, J=7.1 Hz, 2H, benzoate ortho), 7.64 (m, 2H, aromatic), 7.60 (m, 1H, aromatic), 7.49 (m, 9H, aromatic), 7.03 (d, J=8.8 Hz, 1H, NH), 6.26 (s, 1H, H10), 6.21 (dd, J=8.2, 8.2 Hz, 1H, H13), 5.76 (dd, J=8.8, 2.2 Hz, 1H, H3'), 5.66 (d, J=7.1 Hz, 1H, H2β), 4.92 (dd, J=9.9, 1.1 Hz, 1H, H5), 4.77 (dd, J=5.5, 2.2 Hz, 1H, H2'), 4.38 (m, 1H, H7), 4.29 (d, J=8.8 Hz, 1H, H20α), 4.18 (d, J=8.5 Hz, 1H, H20β), 3.78 (d, J=6.6 Hz, 1H, H3), 3.35 (d, J=5.5 Hz, 1H, 2'OH), 2.55 (m, 1H, H6a), 2.49 (d, J=4.2 Hz, 1H, 7OH), 2.36 (s, 3H, 4Ac), 2.28 (m, 2H, H14), 2.22 (s, 3H, 10Ac), 1.85 (m, 1H, H6β), 1.77 (br s, 3H, Me18), 1.76 (s, 1H, 1OH), 1.67 (s, 3H, Me19), 1.22 (s, 3H, Me17), 1.13 (s, 3H, Me16).

EXAMPLE 29

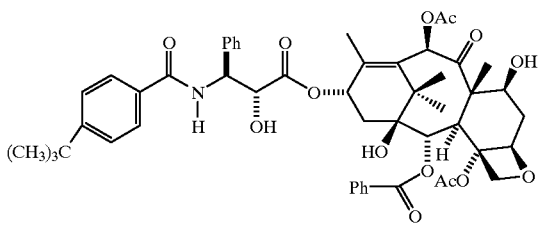

Preparation of N-debenzoyl-N-(4-butylbenzoyl) Taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of (+)-cis-1-(4-t-butylbenzoyl)-3-triethylsilyloxy-4-phenylazetidin-2-one (226 mg, 0.515 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 330 mg of crude (2'R,3'S)-2',7-(bis)triethylsilyl-N-debenzoyl-N-(4-t-butylbenzoyl) taxol.

To a solution of 330 mg (0.289 mmol) of this crude product in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 240 mg (92%) of N-debenzoyl-N-(4-t-butylbenzoyl) taxol, which was recrystallized from methanol/water. m.p. 171–173° C; [α]²⁵_Na −49.1° (c 0.05, CHCl₃).

¹H NMR (CDCl₃, 300 MHz) δ 8.13 (d, J=7.1 Hz, 2H, benzoate ortho), 7.76–7.25 (m, 12H, aromatic), 6.98 (d, J=8.8 Hz, 1H, NH), 6.27 (s, 1H, H10), 6.21 (dd, J=8.8, 8.8 Hz, 1H, H13), 5.77 (dd, J=8.8, 2.7 Hz, 1H, H3'), 5.67 (d, J=6.6 Hz, 1H, H2β), 4.94 (dd, J=9.3, 1.2 Hz, 1H, H5), 4.78 (dd, J=4.4, 2.7 Hz, 1H, H2'), 4.38 (m, 1H, H7), 4.29 (d, J=8.2 Hz, 1H, H20α), 4.20 (d, J=8.2 Hz, 1H, H20β), 3.79 (d, J=6.6 Hz, 1H, H3), 3.65 (d, J=4.4 Hz, 1H, 2'OH), 2.57 (m, 1H, H6α), 2.48 (d, J=4.1 Hz, 1H, 7OH), 2.37 (s, 3H, 4Ac), 2.31 (m, 2H, H14), 2.22 (s, 3H, 10Ac), 1.85 (m, 1H, H6β), 1.79 (br s, 3H, Me18), 1.68 (s, 1H, 1OH), 1.68 (s, 3H, Me19), 1.29 (s, 9H, Ar'Bu), 1.23 (s, 3H, Me17), 1.13 (s, 3H, Me16).

EXAMPLE 30

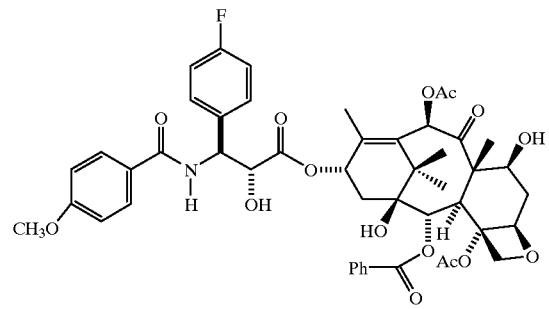

Preparation of N-debenzoyl-N-(4-methoxybenzoyl)-3'-desphenyl-3'-(4-fluorophenyl) Taxol To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of cis-1-(4-methoxybenzoyl)-3-triethylsilyloxy-4-(4-fluorophenyl)azetidin-2-one (614 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 362 mg of a mixture containing (2'R,3'S)-2',7-(bis)triethylsilyl-N-debenzoyl-N-(4-methoxybenzoyl)-3'-desphenyl-3'-(4-fluorophenyl) taxol and a small amount of the (2'S,3'R) isomer.

To a solution of 362 mg of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 269 mg of material which was purified by flash chromatography to give 183 mg (71%) of N-debenzoyl-N-(4-methoxybenzoyl)-3'-desphenyl-3'-(4-fluorophenyl) taxol, which was recrystallized from methanol/water. m.p. 172.5–174.5° C; [α]²⁵_Na −47.0° (c 0.0044, CHCl₃).

¹H NMR (CDCl₃, 300 MHz) δ 8.13 (d, J=7.2 Hz, 2H, benzoate ortho), 7.7–7.4 (m, 9H, aromatic), 7.10 (dd, J=8.8, 8.8 Hz, 2H, aromatic), 6.97 (d, J=8.8 Hz, 1H, NH), 6.27 (s, 1H, H10), 6.23 (dd, J=8.8, 8.8 Hz, 1H, H13), 5.76 (dd, J=8.8, 2.2 Hz, 1H, H3'), 5.67 (d, J=7.1 Hz, 1H, H2β), 4.94 (dd, J=9.9, 2.2 Hz, 1H, H5), 4.75 (dd, J=4.4, 2.2 Hz, 1H, H2'), 4.39 (m, 1H, H7), 4.31 (d, J=8.5 Hz, 1H, H20a), 4.19 (d, J=8.5 Hz, 1H, H20β), 3.79 (d, J=7.1 Hz, 1H, H3), 3.59 (d, J=4.4 Hz, 1H, 2'OH), 2.54 (m, 1H, H6a), 2.47 (d, J=4.4 Hz, 1H, 7OH), 2.36 (s, 3H, 4Ac), 2.30 (m, 2H, H14α, H14β), 2.24 (s, 3H, 10Ac), 1.88 (m, 1H, H6a), 1.78 (br s, 3H, Me18), 1.74 (s, 1H, 1OH), 1.68 (s, 3H, Me19), 1.23 (s, 3H, Me17), 1.14 (s, 3H, Me16).

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What I claim is:

1. A metal alkoxide having the formula:

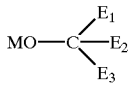

wherein

M is a metal;

$E_1$ and $E_2$ and the carbon to which they are attached define a tricyclic taxane nucleus; and $E_3$ is hydrogen or hydrocarbon.

2. The metal alkoxide of claim 1 wherein $E_3$ is hydrogen.

3. The metal alkoxide of claim 2 wherein M is a Group IA, IIA, IIIA, lanthanide, actinide, Group IIIA, IVA, VA, or VIA metal, zinc or cadmium.

4. The metal alkoxide of claim 2 wherein the metal is a Group IA, IIA or transition metal.

5. The metal alkoxide of claim 2 wherein the metal is lithium, magnesium, sodium, potassium or titanium.

6. The metal alkoxide of claim 2 wherein the metal is lithium.

7. An alkoxide having the formula:

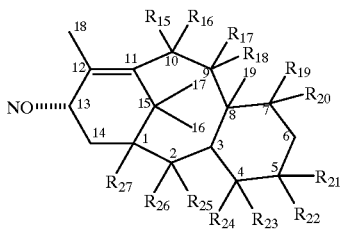

wherein

M is a metal;

$R_{15}$ and $R_{16}$ are independently hydrogen, hydroxy, lower alkanoyloxy, alkenoyloxy, alkynoyloxy, aryloyloxy or $R_{15}$ and $R_{16}$ together form an oxo;

$R_{17}$ and $R_{18}$ are independently hydrogen or lower alkanoyloxy, alkenoyloxy, alkynoyloxy, or aryloyloxy or $R_{17}$ and $R_{18}$ together form an oxo;

$R_{19}$ and $R_{20}$ are independently hydrogen or hydroxy or lower alkanoyloxy, alkenoyloxy, alkynoyloxy, or aryloyloxy;

$R_{21}$ and $R_{22}$ are independently hydrogen or lower alkanoyloxy, alkenoyloxy, alkynoyloxy, or aryloyloxy or $R_{21}$ and $R_{22}$ together form an oxo;

$R_{24}$ is hydrogen or hydroxy- or lower alkanoyloxy, alkenoyloxy, alkynoyloxy, or aryloyloxy; or $R_{23}$ and $R_{24}$ together form an oxo or methylene or $R_{23}$ and $R_{24}$ together with the carbon atom to which they are attached form an oxirane ring;

$R_{25}$ is hydrogen, hydroxy, or lower alkanoyloxy, alkenoyloxy, alkynoyloxy, or aryloyloxy; or $R_{26}$ is hydrogen, hydroxy, or lower alkanoyloxy, alkenoyloxy, alkynoyloxy, or aryloyloxy; or $R_{26}$ and $R_{25}$ taken together form an oxo; and $R_{27}$ is hydrogen, hydroxy or lower alkoxy, alkanoyloxy, alkenoyloxy, alkynoyloxy, or aryloyloxy.

8. The alkoxide of claim 7 wherein $R_{19}$ is hydrogen;

$R_{20}$ is hydroxy or lower alkanoyloxy, alkenoyloxy, alkynoyloxy, or aryloyloxy;

$R_{21}$ is hydrogen or together with $R_{22}$ forms an oxo;

$R_{22}$ is hydrogen or lower alkanoyloxy, alkenoyloxy, alkynoyloxy, or aryloyloxy or together with $R_{21}$ forms an oxo;

$R_{24}$ is hydrogen or hydroxy or lower alkanoyloxy, alkenoyloxy, alkynoyloxy, or aryloyloxy; or $R_{23}$ and $R_{24}$ together form an oxo or methylene; or $R_{23}$ and $R_{24}$ together with the carbon atom to which they are attached form an oxirane ring; and $R_{25}$ is hydrogen, hydroxy, or lower alkanoyloxy, alkenoyloxy, alkynoyloxy, or aryloyloxy; and $R_{26}$ is hydrogen.

9. The alkoxide of claim 7 wherein $R_{15}$, $R_{17}$, $R_{19}$, $R_{21}$, and $R_{26}$ are hydrogen.

10. The alkoxide of claim 7 wherein $R_{15}$ is hydrogen, and $R_{16}$ is hydroxy or lower alkanoyloxy, alkenoyloxy, alkynoyloxy, or aryloyloxy.

11. The alkoxide of claim 7 wherein $R_{15}$ is hydrogen, and $R_{16}$ is lower alkanoyloxy.

12. The alkoxide of claim 7 wherein $R_{17}$ and $R_{18}$ are hydrogen.

13. The alkoxide of claim 7 wherein $R_{17}$ together with $R_{18}$ forms an oxo.

14. The alkoxide of claim 7 wherein $R_{17}$ is hydrogen, and $R_{18}$ is lower alkanoyloxy, alkenoyloxy, alkynoyloxy, or aryloyloxy.

15. The alkoxide of claim 7 wherein $R_{19}$ is hydrogen, and $R_{20}$ is hydroxy or lower alkanoyloxy, alkenoyloxy, alkynoyloxy, or aryloyloxy.

16. The alkoxide of claim 7 wherein $R_{19}$ and $R_{20}$ are hydrogen.

17. The alkoxide of claim 7 wherein $R_{21}$ is hydrogen, and $R_{22}$ is lower alkanoyloxy, alkenoyloxy, alkynoyloxy or aryloyloxy.

18. The alkoxide of claim 7 wherein $R_{21}$ and $R_{22}$ are hydrogen.

19. The alkoxide of claim 7 wherein $R_{21}$ and $R_{22}$ are independently hydrogen or lower alkanoyloxy, alkenoyloxy, alkynoyloxy, or aryloyloxy or $R_{21}$ and $R_{22}$ together form an oxo;

$R_{24}$ is hydrogen or hydroxy or lower alkanoyloxy, alkenoyloxy, alkynoyloxy, or aryloyloxy; or $R_{23}$ and $R_{24}$ together form an oxo or methylene; or $R_{23}$ and $R_{24}$ together with the carbon atom to which they are attached form an oxirane ring.

20. The alkoxide of claim 7 wherein $R_{24}$ is hydroxy or lower alkanoyloxy, alkenoyloxy, alkynoyloxy, or aryloyloxy.

21. The alkoxide of claim 7 wherein $R_{24}$ is lower alkanoyloxy.

22. The alkoxide of claim 7 wherein $R_{25}$ is hydroxy or lower alkanoyloxy, alkenoyloxy, alkynoyloxy, or aryloyloxy, and $R_{26}$ is hydrogen.

23. The alkoxide of claim 7 wherein $R_{25}$ is lower aryloyloxy, and $R_{26}$ is hydrogen.

24. The alkoxide of claim 7 wherein $R_{24}$ is lower alkanoyloxy, $R_{25}$ is lower aryloyloxy, and $R_{26}$ is hydrogen.

25. The alkoxide of claim 7 wherein $R_{27}$ is $R_{27}$ is hydroxy or lower alkoxy, alkanoyloxy, alkenoyloxy, alkynoyloxy, or aryloyloxy.

26. The alkoxide of claim 7 wherein $R_{15}$ is hydrogen;

$R_{16}$ is hydroxy or lower alkoxy, alkanoyloxy, alkenoyloxy, alkynoyloxy, or aryloyloxy;

$R_{17}$ together with $R_{18}$ form an oxo;

$R_{19}$ is hydrogen;

$R_{20}$ is hydroxy or lower alkoxy, alkanoyloxy, alkenoyloxy, alkynoyloxy, or aryloyloxy;

$R_{24}$ is acetoxy;

$R_{25}$ is benzoyloxy; and $R_{27}$ is hydroxy.

27. The metal alkoxide of claim 7 wherein M is a Group IA, IIA, IIIA, lanthanide, actinide, Group IIIA, IVA, VA, or VIA metal, zinc or cadmium.

28. The metal alkoxide of claim 7 wherein the metal is a Group IA, IIA or transition metal.

29. The metal alkoxide of claim 7 wherein the metal is lithium, magnesium, sodium, potassium or titanium.

30. The metal alkoxide of claim 7 wherein the metal is lithium.

31. An alkoxide having the formula:

[chemical structure diagram]

wherein

M is a metal;

$R_{16}$ is hydrogen, hydroxy, lower alkanoyloxy, alkenoyloxy, alkynoyloxy or aryloyloxy, or oxo;

$R_{18}$ is hydrogen, lower alkanoyloxy, alkenoyloxy, alkynoyloxy or aryloyloxy, or oxo;

$R_{20}$ is hydrogen, hydroxy, lower alkanoyloxy, alkenoyloxy, alkynoyloxy or aryloyloxy;

$R_{21}$ and $R_{22}$ are independently hydrogen or lower alkanoyloxy, alkenoyloxy, alkynoyloxy, or aryloyloxy or $R_{21}$ and $R_{22}$ together form an oxo;

$R_{24}$ is hydrogen or hydroxy or lower alkanoyloxy, alkenoyloxy, alkynoyloxy, or aryloyloxy; or $R_{23}$ and $R_{24}$ together form an oxo or methylene; or $R_{23}$ and $R_{24}$ together with the carbon atom to which they are attached form an oxirane ring; and $R_{25}$ is hydrogen, hydroxy, lower alkanoyloxy, alkenoyloxy, alkynoyloxy or aryloyloxy, or oxo; and $R_{27}$ is hydrogen, hydroxy, lower alkanoyloxy, alkenoyloxy, alkynoyloxy or aryloyloxy.

32. The alkoxide of claim 31 wherein $R_{21}$ is hydrogen or together with $R_{22}$ forms an oxo.

33. The alkoxide of claim 31 wherein $R_{16}$ is lower alkanoyloxy, alkenoyloxy, alkynoyloxy or aryloyloxy.

34. The alkoxide of claim 31 wherein $R_{16}$ is lower alkanoyloxy.

35. The alkoxide of claim 31 wherein $R_{18}$ is hydrogen or lower alkanoyloxy, alkenoyloxy, alkynoyloxy, or aryloyloxy.

36. The alkoxide of claim 31 wherein $R_{18}$ is oxo.

37. The alkoxide of claim 31 wherein $R_{20}$ is hydrogen or hydroxy.

38. The alkoxide of claim 31 wherein $R_{20}$ is lower alkanoyloxy, alkenoyloxy, alkynoyloxy, or aryloyloxy.

39. The alkoxide of claim 31 wherein $R_{22}$ is lower alkanoyloxy, alkenoyloxy, alkynoyloxy, or aryloyloxy.

40. The alkoxide of claim 31 wherein $R_{21}$ is hydrogen, and $R_{22}$ is lower alkanoyloxy, alkenoyloxy, alkynoyloxy, or aryloyloxy.

41. The alkoxide of claim 31 wherein $R_{24}$ is hydrogen or hydroxy.

42. The alkoxide of claim 31 wherein $R_{24}$ is lower alkanoyloxy, alkenoyloxy, alkynoyloxy, or aryloyloxy.

43. The alkoxide of claim 31 wherein $R_{24}$ is lower alkanoyloxy.

44. The alkoxide of claim 31 wherein $R_{25}$ is hydrogen or hydroxy.

45. The alkoxide of claim 31 wherein $R_{25}$ is lower alkanoyloxy, alkenoyloxy, alkynoyloxy, or aryloyloxy.

46. The alkoxide of claim 31 wherein $R_{25}$ is lower aryloyloxy.

47. The alkoxide of claim 31 wherein $R_{24}$ is lower alkanoyloxy, and $R_{25}$ is lower aryloyloxy.

48. The alkoxide of claim 31 wherein $R_{27}$ is hydroxy or lower alkanoyloxy, alkenoyloxy, alkynoyloxy, or aryloyloxy.

49. The alkoxide of claim 31 wherein $R_{16}$ is hydroxy or lower alkanoyloxy, alkenoyloxy, alkynoyloxy, or aryloyloxy;

$R_{16}$ is oxo;

$R_{20}$ is hydroxy or lower alkanoyloxy, alkenoyloxy, alkynoyloxy, or aryloyloxy;

$R_{24}$ is acetoxy;

$R_{25}$ is benzoyloxy; and $R_{27}$ is hydroxy.

50. The metal alkoxide of claim 31 wherein M is a Group IA, IIA, IIIA, lanthanide, actinide, Group IIIA, IVA, VA, or VIA metal, zinc or cadmium.

51. The metal alkoxide of claim 31 wherein the metal is a Group IA, IIA or transition metal.

52. The metal alkoxide of claim 31 wherein the metal is lithium, magnesium, sodium, potassium or titanium.

53. The metal alkoxide of claim 31 wherein the metal is lithium.

\* \* \* \* \*

UNITED STATES PATENT AND TRADEMARK OFFICE
CERTIFICATE OF CORRECTION

PATENT NO.   : 6,069,260
DATED        : May 30, 2000
INVENTOR(S)  : Robert A. Holton It is certified that error appears in the above-identified patent and that said Letters Patent is hereby corrected as shown below:

Column 1,
Line 16, before "BACKGROUND OF THE INVENTION" please add the following paragraph:

-- This invention was made with Government support under NIH Grant #CA 42031 awarded by the National Institutes of Health. The Government has certain rights in the invention. --

Column 14,
Lines 35-40, structure (2) should read:

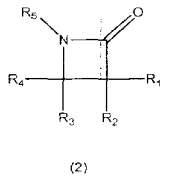

(2)

Column 19,
Line 62, "3'-desphenyl-3'-(-napthyl)" should read -- 3'-desphenyl-3'-(1-napthyl) --.

Column 28,
Line 20, "3'-desphenyl-31-(4-fluorophenyl)" should read -- 3'-desphenyl-3'-(4-fluorophenyl) --.

Column 35,
Line 28, "N-debenzoyl-N-(4-butylbenzoyl)" should read -- N-debenzoyl-N-(4-t-butylbenzoyl) --.

Column 37,
Lines 26-34, the chemical structure should read:

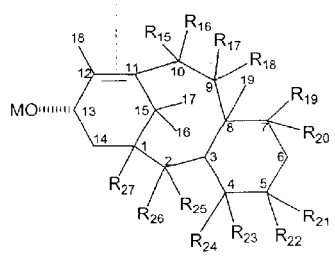

Line 51, "hydroxy-" should read -- hydroxy --.

UNITED STATES PATENT AND TRADEMARK OFFICE
CERTIFICATE OF CORRECTION

PATENT NO. : 6,069,260
DATED : May 30, 2000
INVENTOR(S) : Robert A. Holton

It is certified that error appears in the above-identified patent and that said Letters Patent is hereby corrected as shown below:

Column 38,
Line 60, delete the second instance of "$R_{27}$ is".

Signed and Sealed this

Thirty-first Day of August, 2004

JON W. DUDAS
*Director of the United States Patent and Trademark Office*